US009733179B1

(12) United States Patent
Bugbee

(10) Patent No.: US 9,733,179 B1
(45) Date of Patent: Aug. 15, 2017

(54) CHLOROPHYLL METERS AND RELATED METHOD

(71) Applicant: Apogee Instruments, Inc., Logan, UT (US)

(72) Inventor: Bruce Bugbee, Logan, UT (US)

(73) Assignee: APOGEE INSTRUMENTS, INC., Logan, UT (US)

( * ) Notice: Subject to any disclaimer, the term of this patent is extended or adjusted under 35 U.S.C. 154(b) by 34 days.

(21) Appl. No.: 14/730,070

(22) Filed: Jun. 3, 2015

Related U.S. Application Data

(60) Provisional application No. 62/007,843, filed on Jun. 4, 2014.

(51) Int. Cl.
- *G01N 21/00* (2006.01)
- *G01N 21/31* (2006.01)
- *G01N 33/00* (2006.01)

(52) U.S. Cl.
CPC ......... *G01N 21/31* (2013.01); *G01N 33/0098* (2013.01); *G01N 2201/062* (2013.01); *G01N 2201/12* (2013.01)

(58) Field of Classification Search
CPC ..... G01N 2021/635; G01N 2021/8466; G01N 2021/6419; G01N 2021/6421; G01N 2021/1736; G01N 21/3151; G01N 33/025; G01N 33/0098; G01J 3/10; G01J 3/42
USPC .... 356/432–440, 420, 51, 73, 419, 319, 307
See application file for complete search history.

(56) References Cited

U.S. PATENT DOCUMENTS

| | | | | |
|---|---|---|---|---|
| 4,295,042 A | * | 10/1981 | Watanabe | G01N 21/314 250/226 |
| 6,020,587 A | * | 2/2000 | Spiering | G01N 21/314 250/339.11 |
| 7,746,452 B2 | | 6/2010 | Fuchigami et al. | |
| 8,257,982 B2 | * | 9/2012 | Cerovic | G01N 21/3151 356/17 |

(Continued)

OTHER PUBLICATIONS

Apogee Instruments, Owner's Manual for Chlorophyll Content Meter model CCM-200 Plus, (available as early as 1999), 20 pages.

(Continued)

*Primary Examiner* — Hoa Pham
(74) *Attorney, Agent, or Firm* — TraskBritt

(57) ABSTRACT

A method, system, and apparatus for determining chlorophyll content of a plant sample. The method includes emitting light at a first wavelength and a second wavelength into a plant sample with a chlorophyll meter; detecting the light after passing through the plant sample; generating an optical value responsive to a ratio of the percentage of transmitted light through the plant sample for the first wavelength and the second wavelength; and determining chlorophyll content based on the optical value compared with an optical/absolute chlorophyll relationship that was determined by a matched combination of extraction method, extraction solvent, spectrophotometric equation, and spectrophotometer resolution, wherein the optical/absolute relationship is one of a plurality of different optical/absolute relationships that a user may select from for different species. These relationships may link in situ optical measurements with in vitro chlorophyll concentration for display on a chlorophyll meter in units of mass or moles of chlorophyll per unit area or mass of tissue.

17 Claims, 13 Drawing Sheets

(56) References Cited

U.S. PATENT DOCUMENTS

| | | | | |
|---|---|---|---|---|
| 9,075,008 B2* | 7/2015 | Holland | ............... | G01J 3/10 |
| 2008/0239293 A1* | 10/2008 | Fuchigami | ......... | G01N 21/3151 |
| | | | | 356/73 |
| 2013/0342844 A1* | 12/2013 | Tixier | ............... | C12N 1/14 |
| | | | | 356/409 |
| 2015/0330898 A1* | 11/2015 | Choi | ............... | C12Q 1/04 |
| | | | | 435/34 |

OTHER PUBLICATIONS

Atkinson et al., Effects of Cultivar, Fruit Number and Reflected Photosynthetically Active Radiation on Fragaria x ananassa Productivity and Fruit Ellagic Acid and Ascorbic Acid Concentrations, Annals of Botany, 97(3):429-441, 2006, 13 pages.
Force A., Owner's Manual for Dualex Scientific optical leaf-clip, (available as early as 2004), 25 pages.
Liberloo et al, Photosynthetic stimulation under long-term CO2 enrichment and fertilization is sustained across a closed Populus canopy profile (EUROFACE). New Phytologist, 173(3):53x 549, 2007, 13 pages.
Opti-Sciences Inc., Brochure for Chlorophyll Content Meter model CCM-200 Plus, (available as early as 2005), 2 pages.
Opti-Sciences Inc., Brochure for Chlorophyll Content Meter model CCM-300, (available as early as 2011), 2 pages.
Parry et al., In situ measurement of leaf chlorophyll concentration: analysis of the optical/absolute relationship. Plant and Cell Environment 37:250x 2520, 2014, 13 pages.
Spectrum Technologies Inc., Product Manual for SPAD 502 Plus Chlorophyll Meter, (available as early as 2011) 24 pages.
Tegelberg et al., Red:far-red light ratio and UV-B radiation: Their effects on leaf phenolics and growth of silver birch seedlings. Plant, Cell & Environment, 27(8):1005-1013, 2004, 9 pages.

\* cited by examiner ent entitled
CHLOROPHYLL METERS AND RELATED METHOD

CROSS-REFERENCE TO RELATED APPLICATION

This application claims the benefit of U.S. Provisional Patent Application Ser. No. 62/007,843, filed Jun. 4, 2014, the disclosure of which is hereby incorporated herein in its entirety by this reference. It is noted that a document entitled "In situ measurement of leaf chlorophyll concentration: Analysis of the optical/absolute relationship," by Christopher Parry, J. Mark Blonquist, and Bruce Bugbee was attached to the provisional patent application to form part of the original disclosure (Appendix A). Thus, this document is also incorporated herein in its entirety by this reference.

TECHNICAL FIELD

Embodiments of the disclosure relate generally to chlorophyll meters, and in particular, to apparatuses and methods to achieve in situ measurement of chlorophyll content of a plant.

BACKGROUND

Chlorophyll is a green pigment found in plant cells, algae cells, and cyanobacteria. The primary function of chlorophyll molecules is radiation absorption, which provides energy for photosynthesis. Measuring chlorophyll in plants (e.g., primarily leaves of plants) may be helpful in determining if the plant has proper conditions (e.g., habitat, nutrients, lighting, etc.) for optimum growth. For example, when unfavorable growth conditions result in plant physiological stress, leaf chlorophyll content often begins to decrease. Thus, chlorophyll measurements may be useful in the detection of plant physiological stresses, which may be a result of drought, chemicals (e.g., herbicides), biological influences, or other influences. As a result, early detection of such reduction of chlorophyll may provide an opportunity to identify and reverse the physiological stresses on the plant.

Leaf chlorophyll concentration is generally most accurately measured by extraction of chlorophyll in a solvent followed by in vitro measurements in a spectrophotometer. However, non-destructive, in situ, optical techniques have become widely used to provide a relative indication of leaf chlorophyll concentration. Some optical techniques include monitoring the reflectance of light incident on a plant sample, such as with U.S. Pat. No. 6,020,587 (Spiering et al.) that describes using two light sources with different wavelengths and detecting reflected light from a plant sample to obtain an estimate of chlorophyll content. Another optical technique includes monitoring the transmittance of light after passing through a plant sample, such as with U.S. Pat. No. 7,746,452 (Fuchigami et al.) that describes using light sources with different wavelengths and detecting light transmitted through the plant sample to obtain an estimate of that is representative of chlorophyll content.

Such handheld chlorophyll meters are widely used to estimate leaf chlorophyll concentration as an alternative to destructive sampling techniques, but non-uniform chlorophyll distribution causes the optical measurement to vary widely among species for the same chlorophyll concentration. Over 30 studies to date have sought to quantify the in situ/in vitro (optical/absolute) relationship, but neither chlorophyll extraction nor measurement techniques for in vitro analysis have been consistent among the different studies. In addition, the reported optical/absolute chlorophyll concentration relationship has varied widely, sometimes even within the same species of plants.

Two commercially available chlorophyll meters are currently widely used (e.g., Minolta, model SPAD-502; and Opti-Sciences, model CCM-200). Such commercially available chlorophyll meters output values related to chlorophyll content that are unique to the devices, but these meters do not output values that are in units of chlorophyll content. For example, the Minolta chlorophyll meter displays an output that is a "SPAD" value, while the Opti-Sciences meter displays an output as a "CCI" value. The SPAD values and CCI values are influenced by the chlorophyll content; however, they do not have a linear relationship with the absolute chlorophyll concentration. In other words, a SPAD value of 20 would not necessarily correspond to approximately twice the chlorophyll content as a SPAD value of 10. As a result, users may merely know that chlorophyll content is high or low based on one SPAD value being compared relative to another SPAD value; however, the user may not know the actual amount by which the chlorophyll content actually differs when comparing different SPAD values. CCI values have similar limitations. These SPAD values and CCI values are discussed in further detail below.

SUMMARY

In one embodiment, a chlorophyll meter, comprises a first light source configured to emit light having a first wavelength; a second light source configured to emit light having a second wavelength; a detector configured to: detect the light from the first light source and the second light source transmitted through a plant sample; generate a first data signal indicative of the light transmitted through the plant sample at the first wavelength; and generate a second data signal indicative of the light transmitted through the plant sample at the second wavelength; a processor operably coupled with the first light source, the second light source, and the detector, wherein the processor is configured to generate a chlorophyll content output based on an optical/absolute relationship that is determined by a matched combination of extraction method, extraction solvent, spectrophotometric equation, and spectrophotometer resolution to provide a plurality of different optical/absolute relationships among different species.

In another embodiment, a method for determining chlorophyll content of a plant sample comprises: emitting light at a first wavelength and a second wavelength into a plant sample; detecting the light after passing through the plant sample; generating, with a processor, an optical value responsive to a ratio of the percentage of transmitted light through the plant sample for both the first wavelength and the second wavelength; and determining, with the processor, chlorophyll content based on the optical value compared with an optical/absolute chlorophyll relationship that was determined by a matched combination of extraction method, extraction solvent, spectrophotometric equation, and spectrophotometer resolution, wherein the optical/absolute relationship is one of a plurality of different optical/absolute relationships that a user may select from for different species. In some embodiments, the optical/absolute relationship may be downloaded to the processor.

In another embodiment, a portable optical chlorophyll meter, comprises a sampling head including a plurality of light sources configured to emit different wavelengths of through a plant sample, a detector region including a detector having a field of view aligned with the sampling head to receive the light, the detector configured to detect the different wavelengths of light, an electronic display, and a processor operably coupled with the light sources and the detector. The processor is configured to determine chlorophyll content of the plant sample based on an optical/absolute relationship that is selectable by the user from among optical/absolute relationships stored in memory for a plurality of different plant species, and to display the chlorophyll content on the electronic display in units of chlorophyll (e.g., mass or moles of chlorophyll per unit area or mass of tissue).

DETAILED DESCRIPTION

Figure 1A:
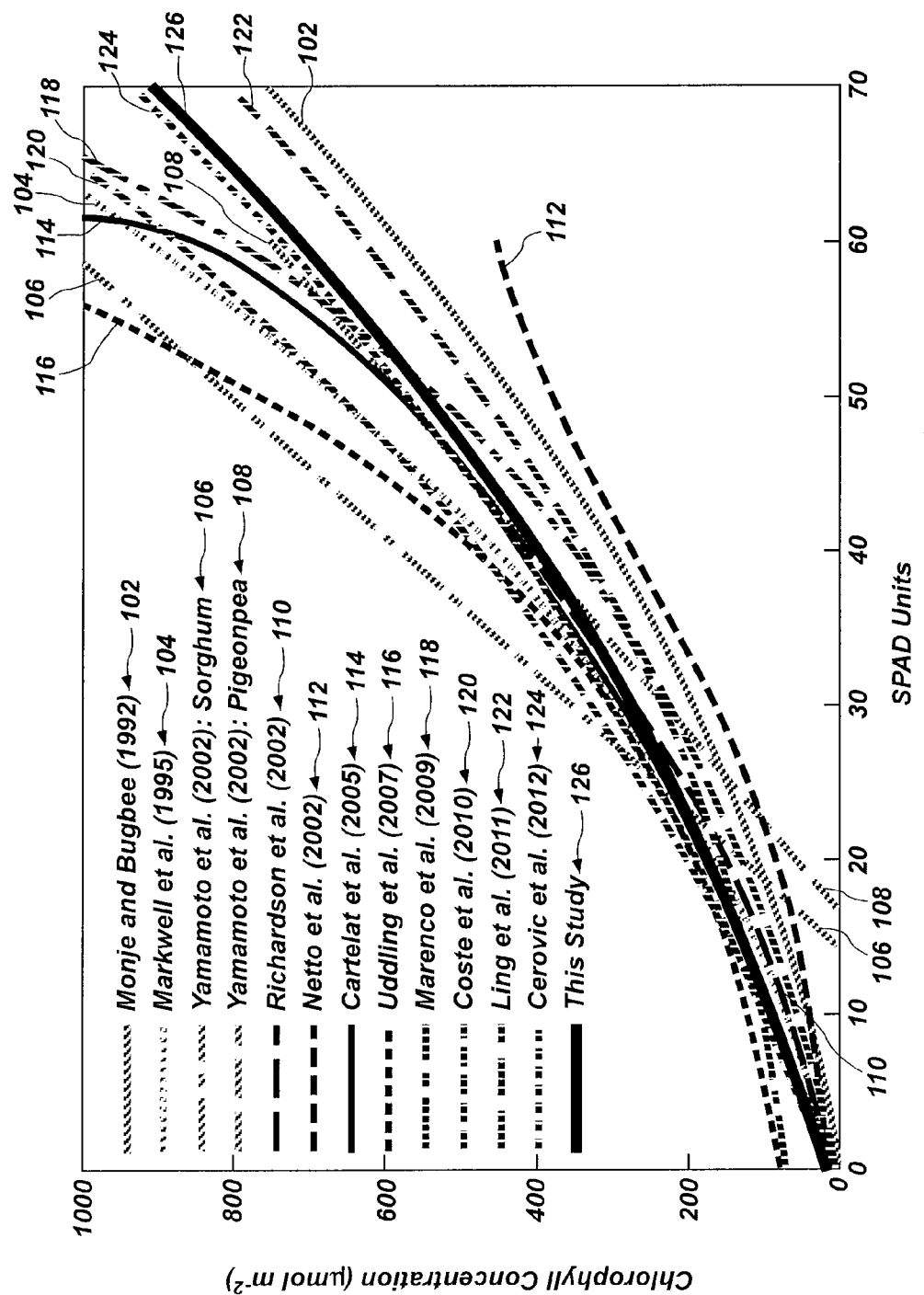
FIGS. 1A and 1B show examples of the non-linear relationship between meter output and chlorophyll concentration based on data for multiple species in multiple studies. The units of chlorophyll content in this example are shown as µmol of chlorophyll per $m^2$ of leaf area.

As noted above, a document entitled "In situ measurement of leaf chlorophyll concentration: Analysis of the optical/absolute relationship," by Christopher Parry, J. Mark Blonquist, and Bruce Bugbee was attached to the provisional patent application as Appendix A. This document resulted in the publication of Parry et al., *In situ measurement of leaf chlorophyll concentration: analysis of the optical/absolute relationship*, Plant Cell Environ. 37, 2508-2520 (2014) (hereinafter "Parry et al."), which is also incorporated herein in its entirety by this reference.

Embodiments of the disclosure include improved chlorophyll meters and related methods for a more accurate determination of chlorophyll content (e.g., density) of a plant sample than current methods using optical meters. Embodiments of the disclosure may be incorporated in a portable handheld chlorophyll meter for sampling plants in situ to obtain an immediate, accurate reading of chlorophyll content. In particular, a plurality of equations defining the optical/absolute relationships may be incorporated within the chlorophyll meter. These equations have been developed to more rigorously link in situ optical measurements with in vitro chlorophyll concentration. Thus, embodiments of the disclosure may include an improved chlorophyll meter that provides the user with more insight to strategies for single-leaf radiation capture among diverse species.

In the following detailed description, reference is made to the accompanying drawings which form a part hereof and, in which are shown by way of illustration, specific embodiments in which the disclosure may be practiced. These embodiments are described in sufficient detail to enable those of ordinary skill in the art to practice the disclosure, and it is to be understood that other embodiments may be utilized, and that structural, logical, and electrical changes may be made within the scope of the disclosure.

In this description, specific implementations are shown and described only as examples and should not be construed as the only way to implement the disclosure unless specified otherwise herein. It will be readily apparent to one of ordinary skill in the art that the various embodiments of the disclosure may be practiced by numerous other partitioning solutions. For the most part, details concerning timing considerations and the like have been omitted where such details are not necessary to obtain a complete understanding of the disclosure and are within the abilities of persons of ordinary skill in the relevant art.

Referring in general to the following description and accompanying drawings, various embodiments of the disclosure are illustrated to show its structure and method of operation. Common elements of the illustrated embodiments may be designated with similar reference numerals. It should be understood that the figures presented are not meant to be illustrative of actual views of any particular portion of the actual structure or method, but are merely idealized representations employed to more clearly and fully depict the invention defined by the claims below.

It should be further appreciated and understood that the various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and steps are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

A processor herein may be any processor, controller, microcontroller, or state machine suitable for carrying out processes of the disclosure. A processor may also be implemented as a combination of computing devices, such as a combination of a DSP and a microprocessor, a plurality of microprocessors, one or more microprocessors in conjunction with a DSP core, or any other such configuration. When configured according to embodiments of the disclosure, a special-purpose computer improves the function of a general-purpose computer because, absent the disclosure, the general-purpose computer would not be able to carry out the processes of the disclosure. The disclosure also provides meaningful limitations in one or more particular technical environments that go beyond an abstract idea. For example, embodiments of the disclosure provide improvements in the technical field of optical chlorophyll content measurement and reporting, and in particular developing methods that improve the operation of such chlorophyll meters such that a new chlorophyll meter has been developed.

The term "plant" as used herein includes matter that contains chlorophyll, which includes land plants, algae, and cyanobacteria. These organisms are sometimes referred to as a "plant sample."

The acronym "SPAD" refers to a division of Minolta (Special Products Analysis Division) that developed the SPAD line of chlorophyll meters. As the name implies, the acronym "SPAD" itself has no direct meaning related to chlorophyll concentration. The disclosure refers to SPAD values (also referred to as SPAD units) as the output of a SPAD meter according to the confidential equation of Minolta, which is described below with reference to equation (2).

The term "absolute" when referring to chlorophyll measurements refers to values that are derived from analysis performed on a plant sample in vitro, which may involve placing a plant sample within a solvent to extract the chlorophyll from the plant sample. As per standard analytical techniques, "absolute" refers to a measured value that referenced to a calibration standard. It does not imply that the value is 100% accurate of the amount of chlorophyll. As discussed below, there may be variations in the "absolute" chlorophyll content value of the same plant sample depending on the methods and calculations used.

In the disclosure 1) standard procedures for measurement of chlorophyll are reviewed, 2) the error associated with non-standard procedures is discussed, and 3) example equations for conversion of optical to absolute chlorophyll for at least 22 individual species grown in multiple environments are provided to be implemented by chlorophyll meters according to embodiments of the disclosure. Application of such chlorophyll meters may include chlorophyll concentration determination for plant nutrient assessment, environmental stress impact, fertilizer application or equipment, among other uses.

Tests of five Minolta (model SPAD-502) and 25 Opti-Sciences (model CCM-200) meters, manufactured from 1992 to 2013, indicate that differences among replicate models are less than 5%. Equations for converting between units from these meter types have been developed for implementation by chlorophyll meters. Embodiments of the disclosure include a derived relationship between optical transmission ratios and absolute chlorophyll concentration and show how non-uniform distribution among species causes a variable, non-linear response. These results more rigorously link in situ optical measurements with in vitro chlorophyll concentration and provide insight to strategies for single-leaf radiation capture among diverse species.

Measurement of Absolute Chlorophyll Concentration In Vitro

In order to accurately determine chlorophyll in vitro, the extraction method, extraction solvent, spectrophotometric equation, and spectrophotometer resolution should match (Wellburn, 1994). More than 30 studies have been conducted, but few have used the appropriate combination of analytical procedures. Table 1 shows a summary of these publications, including the chlorophyll meter type, authors, year of publication, and species that were studied.

TABLE 1

| Meter Type | Author | Year | Species |
| --- | --- | --- | --- |
| SPAD-501 | Yadava | 1986 | 22 unrelated species |
|  | Marquard and Tipton | 1987 | 12 unrelated species |
|  | Schaper and Chacko | 1991 | eight tropical and subtropical fruit-tree species |
|  | Dwyer et al. | 1991 | Maize |
|  | Fanizza et al. | 1991 | 12 wine-grape cultivars |
| SPAD-502 | Gratani | 1992 | six sclerophyllous species |
|  | Monje and Bugbee | 1992 | rice, soybean, wheat |
|  | Markwell et al. | 1995 | soybean and maize |
|  | Xu et al. | 2000 | sorghum |
|  | Bindi et al. | 2002 | Potato |
|  | Richardson et al. | 2002 | paper birch |
|  | Netto et al. | 2002 | Papaya |
|  | Yamamoto et al. | 2002 | sorghum and pigeonpea |
|  | Esposti et al. | 2003 | four citrus species |
|  | Wang et al. | 2004 | peace lily |
|  | Netto et al. | 2005 | Coffee |
|  | Jifon et al. | 2005 | six citrus species |
|  | Cartelat et al. | 2005 | Wheat |
|  | Uddling et al. | 2007 | birch, wheat, and potato |
|  | Marenco et al. | 2009 | six Amazonian tree species |
|  | Naus et al. | 2010 | tobacco |
|  | Imanishi et al. | 2010 | flowering cherry |
|  | Coste et al. | 2010 | thirteen tree species of tropical rainforest |
|  | Ling et al. | 2011 | *Arabidopsis thaliana* |
|  | Cerovic et al. | 2012 | kiwi, grape, wheat, and maize |
| CCM-200 | Richardson et al. | 2002 | paper birch |
|  | van den Berg and Perkins | 2004 | sugar maple |
|  | Jifon et al. | 2005 | six citrus species |
|  | Goncalves et al. | 2008 | four tropical wood species |
|  | Cerovic et al. | 2012 | kiwi, grape, wheat, and maize |

Six organic solvents have been widely used for chlorophyll extraction: acetone, methanol, chloroform, diethyl-ether, dimethyl-formamide (DMF), and dimethyl-sulphoxide (DMSO). Acetone has been the most widely used solvent because it has sharp chlorophyll peaks, but acetone is considered to be less efficient at chlorophyll extraction than methanol and ethanol (Holmhansen and Riemann, 1978, Ritchie, 2006). These three solvents (acetone, methanol, ethanol) require grinding of leaf tissue for complete extraction of chlorophyll. DMF and DMSO have an advantage over other solvents in that they allow for immersion of intact leaf tissue for chlorophyll extraction. However, immersion may not be effective for all plant tissues. For example, Schaper and Chacko (1991) were not able to completely extract chlorophyll from Cashew and Mango leaf discs using DMSO. DMSO is less toxic than DMF, and extracted solutions may be stable up to 7 days in the dark at 4° C. (Barnes, Balaguer, Manrique, Elvira and Davison, 1992). These advantages have led to increasing use of DMSO as an extraction solvent; however, DMSO is absorbed through the skin and gloves should be worn when handling DMSO (Barnes et al., 1992).

Matching Extraction Solvent with Spectrophotometric Equation to Convert Absorption Values to Chlorophyll Concentration Wellburn (1994) emphasized the importance of using spectrophotometric equations that have been derived from accurate extinction coefficients determined in a reliable reference solution. Extinction coefficients from Smith and Benitez (1955) derived for diethyl-ether are generally accepted as accurate and are recommended for use in deriving extinction coefficients for other extraction solvents using the procedures described in Porra et al. (1989). Based on the magnesium concentration of a known chlorophyll a and b solution, Porra et al. (1989) confirmed the extinction coefficients of Smith and Benitez (1955) for both chlorophyll a and b in diethylether. Porra et al. (1989) found that the error in the original Smith and Benitez (1955) equation was less than 1%. Several equations developed for DMSO and DMF solvents have failed to follow the appropriate Porra et al. (1989) procedure (Barnes et al., 1992, Inskeep and Bloom, 1985, Moran, 1982, Moran and Porath, 1980).

The equations developed by Arnon (1949) have often been used to quantify chlorophyll a and b concentration in higher plants and green algae. These equations were developed for use with 80% acetone in water. Several authors (Barnes et al., 1992, Lichtenthatler and Wellburn, 1983, Porra, 2002) have reported that equations from Arnon (1949) are inaccurate because they used the less accurate extinction coefficients of Mackinney (1941). Also, the chlorophyll a/b ratios obtained from the equations of Arnon (1949) underestimate the true chlorophyll a/b ratio (Porra, Thompson and Kriedemann, 1989, Wellburn, 1994). Porra et al. (1989) developed an equation to convert chlorophyll a/b ratios determined by the equations of Arnon (1949) to correct values.

Several authors have used DMSO as an extracting solvent, but used spectrophotometric chlorophyll equations developed for 80% acetone (Monje and Bugbee, 1992; Richardson et al., 2002). This is has been justified by citing other publications that suggest that absorption spectra for chlorophyll a and b are identical for 90% acetone and DMSO (Hiscox and Israelstam, 1979, Ronen and Galun, 1984, Shoaf and Lium, 1976). However, equations from Arnon (1949) were developed for 80% (not 90%) acetone. Furthermore, Barnes et al. (1992) showed that the peak absorption wavelength for chlorophyll a and b is at a longer wavelength in DMSO than 80% acetone and found that equations from Arnon (1949) underestimated chlorophyll concentration using DMSO extracts by approximately 10%.

Matching Spectrophotometric Chlorophyll Equations with Instrument Resolution

Wellburn (1994) discussed differences in chlorophyll measurement among spectrophotometers with differing spectral bandwidth resolution. Early spectrophotometer models used to derive equations were capable of only 1 nm to 4 nm resolution. High quality modern spectrophotometers have a resolution of 0.1 nm to 0.5 nm and have been used to derive recently developed spectrophotometric chlorophyll equations. Wellburn (1994) compared three types of spectrophotometers (Uvikon model 941 Plus, 0.5 nm resolution; Hewlett-Packard model HP8452A, diode-array 2 nm fixed resolution; and Pye Unicam model SP30, 1 nm to 4 nm variable resolution) and determined chlorophyll concentrations in six solvents. Wellburn omitted data from the diode array spectrophotometer because the data had values that almost always deviated more than 10% from values of the other two instruments. Wellburn (1994) concluded that diode array spectrophotometers are not appropriate for use with equations derived by non-diode array spectrophotometers, and emphasized that equations derived with one spectrophotometer should not be used with a spectrophotometer with a different spectral resolution.

Although the goal of previous studies has been to develop standard curves to convert optical measurements to absolute chlorophyll concentration, measurement techniques vary widely. Predicted chlorophyll concentration from optical measurements of wheat leaves, measured with the same model of meter, has varied up to 80% between studies (Monje and Bugbee, 1992, Uddling, Gelang-Alfredsson, Piikki and Pleijel, 2007). These differences have not been widely acknowledged in the literature.

Optical Meters Used to Determine Chlorophyll Concentration

Two widely-used chlorophyll concentration meters currently in use are the Konica Minolta, model SPAD-502 Plus (Konica Minolta Sensing, Inc., Sakai, Osaka, Japan) and the Opti-Sciences, model CCM-200 plus (Opti-Sciences, Inc., Hudson, N.H., USA). Both chlorophyll meters measure the transmission of two wavelengths of radiation through plant leaves: red at approximately 650 nm, and near infrared (NIR) at approximately 900 nm. Increased chlorophyll concentration increases the absorption of red radiation. All plants transmit a high fraction of NIR radiation because these wavelengths are not absorbed by photoreceptors. Therefore, the transmission of NIR radiation is used as a reference wavelength.

Another hand-held, optical chlorophyll meter was recently introduced, the Dualex 4 Scientific (Dx4) (FORCE-A, Orsay, France). This chlorophyll meter measures the transmission of radiation at 710 nm and 850 nm and converts the measurement into a value of chlorophyll in $\mu g\ cm^{-2}$.

The sampling area also differs between chlorophyll meters. The CCM-200 samples 71 $mm^2$, the SPAD-502 samples 6 $mm^2$ and the Dx4 samples 20 $mm^2$. Larger areas provide a larger spatial average, but smaller areas can measure narrower leaves.

Description of the Optical Differences Between Meters

The output of the CCM-200 meter is the ratio of transmission of radiation from an LED centered at 931 nm to transmission of radiation from an LED centered at 653 nm (CCM-200 user manual). This ratio is defined as the chlorophyll content index (CCI) value.

$$CCI = \frac{\%\ \text{transmission 931 nm}}{\%\ \text{transmission 653 nm}} \qquad (1)$$

The SPAD-502 measures radiation centered at 940 nm and 650 nm (Minolta manual) and output a SPAD value (also referred to as a SPAD unit). The SPAD values returned by the SPAD-502 are relative indicators of chlorophyll concentration, but do not have a direct relationship to absolute chlorophyll concentration.

The equation to convert these measurements to a SPAD value (also referred to as a SPAD unit) has been reported differently in four publications. The most complete equation may be given by Naus et al. (2010):

$$SPAD = k * \log\left(\frac{\% \text{ transmission 940 nm}}{\% \text{ transmission 650 nm}}\right) + C \quad (2)$$

where k is a confidential slope coefficient and C is a confidential offset value. Three other publications have reported less complete equations to calculate the SPAD value. Uddling et al. (2007) reported equation (2) without the C offset. Cerovic et al. (2012) and Markwell et al. (1995) reported equation (2) without either k or C. Because the slope and offset values are confidential, deriving the exact SPAD values may not be performed from transmission measurements unless the slope and offset were revealed. In addition, mathematically deriving a conversion equation between meters may not be performed without these confidential values. However, because both the SPAD values and the CCI are based on a ratio of the transmission at two closely related wavelengths:

$$SPAD \approx k * \log(CCI) + C \quad (3)$$

Studies on the Optical/Absolute Chlorophyll Concentration Relationship

In order to return a value that indicates chlorophyll content, the optical measurements (e.g., SPAD values, CCI values) may be related to an absolute (in vitro) set of chlorophyll content values. Thus, embodiments of the disclosure include chlorophyll meters that transform optical values into values for absolute chlorophyll.

Four studies have reported empirical relationships that relate optical measurements to absolute chlorophyll concentration for a chlorophyll meter (model SPAD-501) that was a predecessor to the SPAD-502 (Fanizza, Dellagatta and Bagnulo, 1991, Marquard and Tipton, 1987, Schaper and Chacko, 1991, Yadava, 1986). The SPAD-501 used slightly different wavelengths and is thus not directly comparable to the SPAD-502.

Monje and Bugbee (1992) appear to have been the first to develop an equation that relates the output from the SPAD-502 to absolute chlorophyll concentration in mg m-2. Since then, numerous other relationships for a range of species have been proposed (Bindi, et al., 2002; Cartelat, et al., 2005; Cerovic et al., 2012; Coste, et al., 2010; Esposti, et al., 2003; Imanishi, et al., 2010; Jifon, et al., 2005; Ling, et al., 2011; Marenco, et al., 2009; Markwell et al., 1995; Naus et al., 2010; Netto, et al., 2005; Netto, et al., 2002; Richardson, et al., 2002; Schaper, et al., 1991; Uddling et al., 2007; Wang, et al., 2004; Xu, et al., 2000, Yamamoto, et al., 2002).

Like SPAD values, CCI values returned by the CCM-200 are only relative indicators of chlorophyll concentration, as CCI has no direct relationship to chlorophyll concentration. Several studies have also developed chlorophyll prediction equations using CCI measurements from the CCM-200 meter (Cerovic et al., 2012, Goncalves, dos Santos Jr. and E. A., 2008, Jifon et al., 2005, Richardson et al., 2002, van den Berg and Perkins, 2004).

Variation in Experimental Techniques Among Studies

Extraction and measurement techniques for obtaining an absolute chlorophyll concentration value have not been consistent among studies that have attempted to relate optical measurements to the absolute values. Because chlorophyll concentration can have significant spatial variation, it may be desirable to remove the leaf disk from exactly the same location as the optical measurement. This precaution has not always been described in experimental procedures. In addition, as discussed above, multiple extraction solvents, measurement wavelengths, spectrophotometric equations, and instruments with varying resolution have been used to measure absolute chlorophyll. As a result, these sampling and measurement differences likely have caused significant variation among studies.

Most studies that have sought to determine the optical/absolute relationship have used only a single meter with the assumption that all chlorophyll meters of the same model are uniform. In an early study, Marquard and Tipton (1987) found 5% differences between two SPAD-501 meters. Markwell et al. (1995), mentioned that three SPAD-502 meters at the same university differed by ±5% and recommended that separate equations be developed for individual meters, but they did not indicate if optics in the chlorophyll meters had been cleaned before use. A comprehensive evaluation of uniformity among replicate meters does not appear to have been done. Two studies have attempted to estimate the prediction error associated with an individual measurement. Richardson et al. (2002) examined the error associated with individual optical measurements for paper birch leaves. They compared CCM-200 and SPAD-502 meters and found similar errors for both meters (19% for the SPAD meter and 20% for the CCM-200 meter). This relative error was calculated by dividing the root mean square error (RMSE) by average chlorophyll concentration across all samples. Cerovic et al. (2012) compared the Dx4 meter to SPAD-502 and CCM-200 meters and reported similar root mean square errors for all three meters.

Differences Among Plant Groups and Species

Related species may share leaf optical properties. Monocots have a larger fraction of vascular tissue per unit surface area and dicots have a thicker adaxial cuticle with more palisade and spongy tissue. Cerovic et al. (2012) measured two monocot and two dicot species, and suggested that optical/absolute chlorophyll relationships could be grouped into separate monocot and dicot categories.

Chlorophyll a/b Ratio

Considering that chlorophyll a and b can be relatively easily distinguished in vitro, there has been a surprising lack of literature reporting differences among species. Few of the 30 studies on the optical/absolute relationship have reported the chlorophyll a/b ratio. Chang and Troughton (1972) pointed out that the chlorophyll a/b ratio can be affected by the species, environment, phase of leaf and plant growth, and nutrient status on the chlorophyll a/b ratio. Their data indicate that chlorophyll a/b ratios are higher in $C_4$ than $C_3$ plants.

Chlorophyll a/b ratios are known to decrease during leaf senescence (Castro and Sanchez-Azofeifa, 2008, Watts and Eley, 1981), but several studies have found that drought stress has no effect on the chlorophyll a/b ratio (Mafakheri, Siosemardeh, Bahramnejad, Struik and Sohrabi, 2010, Martin and Warner, 1984). Several authors have suggested that chlorophyll a/b ratio should increase as leaf nitrogen content decreases, and the data of Kitajima and Hogan (2003) support this conclusion.

Cultivar Differences within a Species

Markwell et al. (1995) developed a single optical/absolute chlorophyll relationship for multiple strains of soybeans and maize, Uddling et al. (2007) found that a single curve could be used for multiple wheat cultivars grown over multiple seasons, and Dwyer et al. (1991) found that six maize (corn) hybrids had similar relationship curves. However, significantly different relationships were observed among citrus cultivars (Jifon et al., 2005). Cate and Perkins (2003), Richardson et al. (2002), and van den Berg and Perkins (2004) have all cautioned against treating a single optical/absolute chlorophyll relationship as universal.

Embodiments of the Disclosure

Embodiments of the disclosure may 1) estimate the magnitude of differences associated with the use of non-standard combinations of solvents and equations, 2) implement methods for chlorophyll measurement to provide improved equations for conversion of optical measurements to absolute chlorophyll concentration, 3) examine uniformity among two meter models (Opti-Sciences, model CCM-200; and Minolta, SPAD-502) manufactured from 1992 to 2013, 4) develop equations for inter-converting between units (Chlorophyll Content Index and SPAD units) from the two most common chlorophyll meters (Opti-Sciences, model CCM-200; and Minolta, SPAD-502), 5) estimate environmental effects on the optical/absolute chlorophyll concentration relationship, and 6) use optical and mathematical principles to better understand the underlying causes of non-linearity in the optical/absolute chlorophyll concentration relationship.

Collection and Extraction of Samples

Leaves of multiple ages and intensity of green color were measured and sampled from 22 plant species (5 monocots and 17 dicots, 11 deciduous species, and 11 annual crop plants) grown in greenhouse and field environments. Leaves were visually selected for a wide range of the intensity of greenness, which varied due to leaf age, position on the plant, and nutrient deficiencies. A common nutrient deficiency was lack of either nitrogen or iron, which was caused by high root-zone pH. Measurements were made near midday to minimize potential effects of light intensity on chloroplast movement.

Using a CCM-200 meter, the CCI values were measured at least three times in the same location on each leaf and then averaged. A leaf disk was extracted from the exact same location as the measurement. Leaf disks were immediately extracted using a number 4 cork borer with an area of 90 $mm^2$ to replicate the area measured by the chlorophyll meter and placed in a vial containing 10 mL of DMSO. Vials were incubated in an oven at 65° C. until all of the chlorophyll was in solution and the disk became transparent. This extraction occurred in less than 30 minutes for some species, but required 3 hours for other species.

After incubation, a 3 mL aliquot was transferred to an optical-grade analysis cell to measure light absorbance at 646.6 nm and 663.6 nm (Porra, 1989 acetone equation), and at 649.1 nm and 665.1 nm (Wellburn, 1994 DMSO equation) using a Shimadzu UV-2401PC spectrophotometer with a resolution of 0.1 nm. Chlorophyll a and b concentrations were determined from spectral measurements using the equations developed by Wellburn (1994) for DMSO and for 0.1 nm to 0.5 nm spectral resolution:

$$\text{Chlorophyll } a \text{ } (\mu g \text{ } mL^{-1}) = 12.47 * A(665.1 \text{ nm}) - 3.62 * A(649.1 \text{ nm}) \quad (4)$$

$$\text{Chlorophyll } b \text{ } (\mu g \text{ } mL^{-1}) = 25.06 * A(649.1 \text{ nm}) - 6.5 * A(665.1 \text{ nm}) \quad (5)$$

Where A is the absorption at the referenced wavelength and chlorophyll a and b are summed to obtain the total chlorophyll concentration.

Because several publications have extracted with DMSO, but incorrectly used the equation of Porra et al. (1989) that was developed for 80% acetone, chlorophyll was calculated using both procedures to determine the magnitude of error between equations.

Uniformity Among Meters

Five replicate Minolta SPAD-502 meters, manufactured from 1992 to 2008, and 25 replicate Opti-Sciences CCM-200 meters, manufactured from 2007 to 2013, were examined for uniformity of output by making replicate measurements on six colored filters. These filters provided a consistent, uniform standard over a range of readings from 2 to 72 CCI units and from 6 to 62 SPAD units. The filters were Roscolux filters: #88, "Light Green," #3204, "Half Blue," #86, Pea Green; #92, "Turquoise"; #89, "Moss Green"; and #4490, "CalColor 90 Green."

Conversion Between Meters

Optical measurements were made in multiple identical locations on leaves of 10 plant species using both a SPAD-502 meter and a CCM-200 meter. These measurements were supplemented with measurements made on 16 Roscolux filters to provide a wide range of SPAD values and CCI values. Measured SPAD values were plotted against corresponding CCI values to obtain a relationship curve for the output of the two meters.

Multiple Wheat Cultivars

Four diverse wheat cultivars (Golden Spire, Lewjain, Greenville, and Wanser) were grown in a greenhouse under three nutrient treatments: optimal nutrient availability, nitrogen deficient, and iron deficient to determine relationships among cultivars and environmental conditions.

Results

Summary of Previous Studies

Relationships between SPAD-502 and CCM-200 meters and absolute chlorophyll concentration from 17 previous studies indicate a wide range of relationships among species. Some reasons for the differences are the result of differences in chlorophyll distribution in the leaf cells of different species, but variations in the analytical methods used for obtaining the absolute chlorophyll measurements have also contributed to the differences.

Figure 1B:
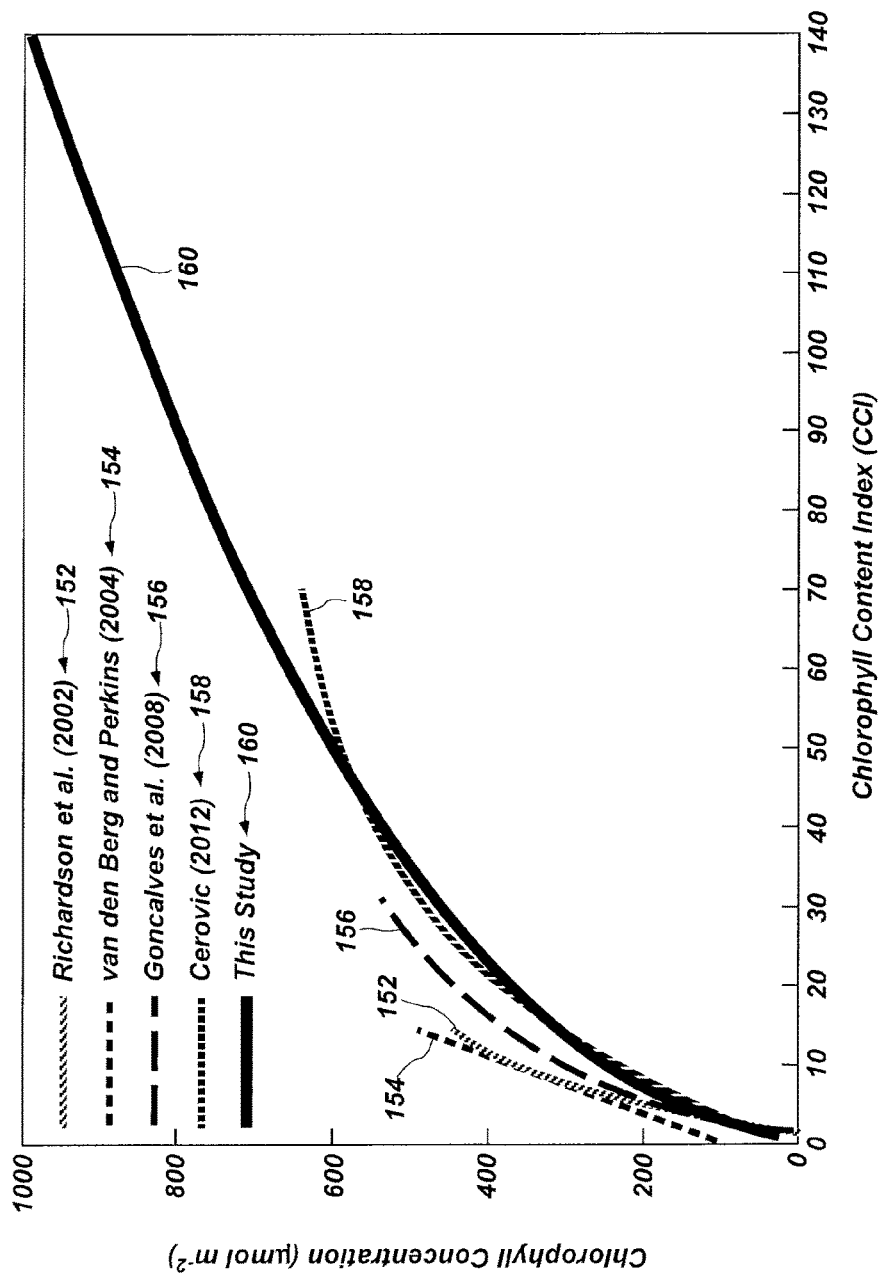

FIGS. 1A and 1B show the optical/absolute relationship between meter output and chlorophyll concentration ($\mu mol$ $m^{-2}$). FIG. 1A shows the relationship results for twelve representative studies (lines 102-124) using SPAD values. In addition, line 126 shows the relationship results using the methods described herein. FIG. 1B shows the relationship results of four representative studies (lines 152-158) using CCI values. In addition, line 160 shows the relationship results using the methods described herein.

Relationships Among Similar Species in Different Studies

Wheat is typically the most widely studied species with four SPAD-502 curves reported in four studies (Cartelat et al., 2005; Cerovic et al., 2012; Monje and Bugbee, 1992; Uddling et al., 2007).

Figure 2:
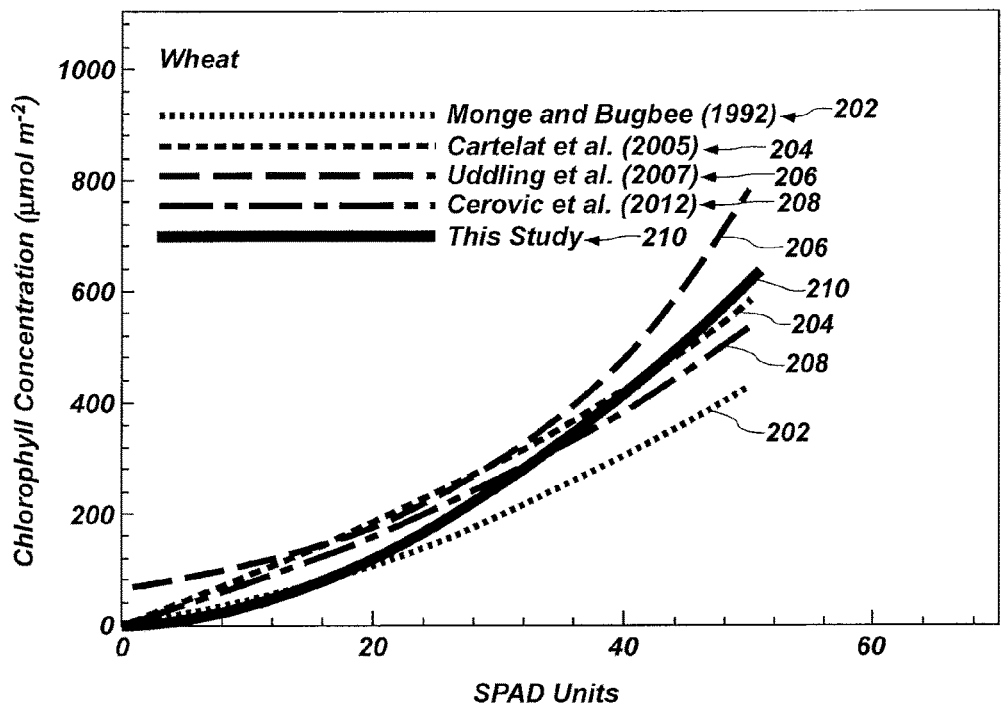
FIG. 2 illustrates an example of the non-linear relationship between SPAD units and chlorophyll concentration (µmol $m^{-2}$) for wheat from four prior studies and this study.

FIG. 2 illustrates the optical/absolute relationship between SPAD units and chlorophyll concentration ($\mu mol$ $m^{-2}$) for wheat. In particular, lines 202-208 show the relationship results from the four listed prior studies. In addition, some measurements have been taken on wheat using methods described herein. A data set was obtained with the SPAD-502 meter, as well as with the CCM-200 meter. The CCI data obtained for the optical/absolute relationship using the methods from this study were converted to SPAD values (using the equation associated with FIG. 7A) in order to develop a comprehensive curve for wheat (line 210). As can be seen in FIG. 2, the measurement using the methods of this disclosure were close to the average of the other studies across all chlorophyll concentrations. No significant difference among cultivars or nutrient stress treatments was found in the optical/absolute chlorophyll relationship for wheat samples.

In addition to wheat, other plant samples have also been studied relative to similar prior studies (data not shown herein). For example, Markwell et al. (1995) contains an optical/absolute relationship curve for soybean, and Yamamoto et al. (2002) contains an optical/absolute relationship curve for sorghum. The mean percentage difference between the optical/absolute relationship curves using methods of this disclosure and their corresponding prior studies was also calculated for these other plant samples. For example, the mean difference between the optical/absolute relationship curve for soybean between Markwell et al. (1995) and the corresponding data related to this disclosure was 29%, and the mean difference between the optical/absolute relationship curve for sorghum between Yamamoto et al. (2002) and the corresponding data related to this disclosure was 40%.

Figure 3:
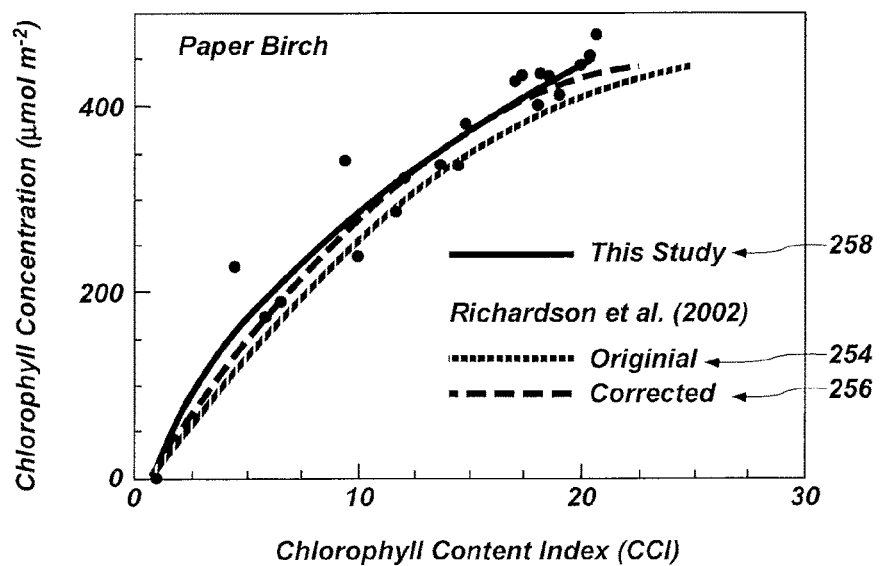
FIG. 3 shows the relationship between chlorophyll content index (CCI) and chlorophyll concentration (µmol $m^{-2}$) for paper birch (*Betula papytifera*) leaves from two studies.

FIG. 3 shows the relationship between CCI data and chlorophyll concentration ($\mu mol\ m^{-2}$) for paper birch (*Betula papytifera*) leaves from two prior studies related to a study of Richardson et al. (2002). The original optical/absolute relationship curve from Richardson et al. (2002) is shown as line 254. This data was corrected based on our determination of the underestimation of chlorophyll concentrations derived from the equation of Porra et al. (1989) for DMSO extractants. This corrected data is shown as line 256.

Paper Birch was the only species that was common among studies using the CCM-200 meter. Richardson et al. (2002) used DMSO as the extractant, and the equation of Porra et al. (1989) that was developed for acetone extractants. We determined the magnitude of the error associated with this incorrect match of extraction solvent and spectrophotometric equation. Based on calculations for each of the 22 individual species performed prior to this disclosure, it was determined that the mean difference between absolute chlorophyll concentrations calculated for a DMSO extractant using the DMSO equation of Wellburn (1994) and the acetone equation of Porra (1989) is approximately 7.84% (Standard deviation 0.28%; data not shown). As a result, the equation from Richardson et al. (2002) for paper birch may be corrected by multiplying it by 7.84%. This correction (line 256) resulted in a nearly identical fit to our derived equation (line 258) for Paper Birch (FIG. 3).

Differences Among Species

Figure 4A:
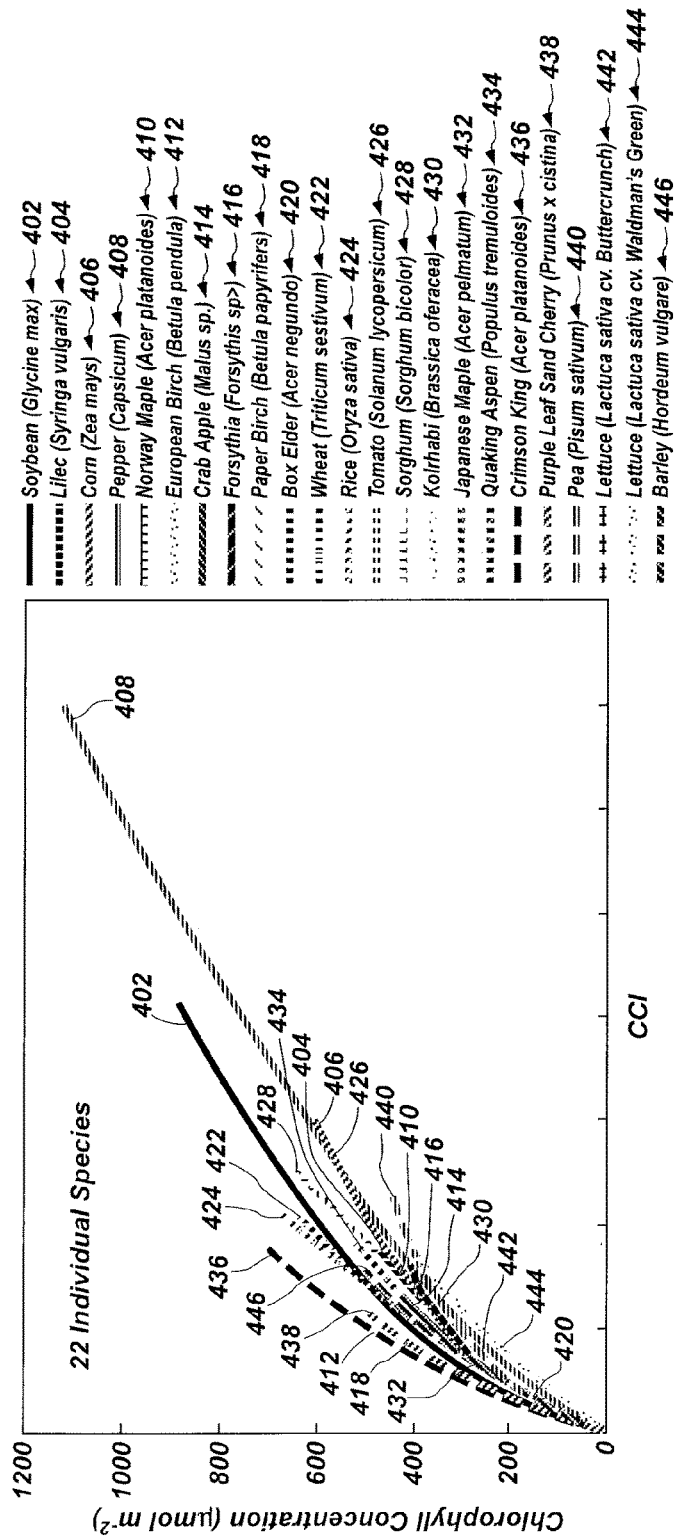
FIGS. 4A and 4B illustrate the relationship between chlorophyll content index (CCI) and chlorophyll concentration (µmol $m^{-2}$) for (FIG. 4A) 22 individual species and (FIG. 4B) all 22 individual species combined. This shows the average degree of non-linearity across species.
Figure 4B:
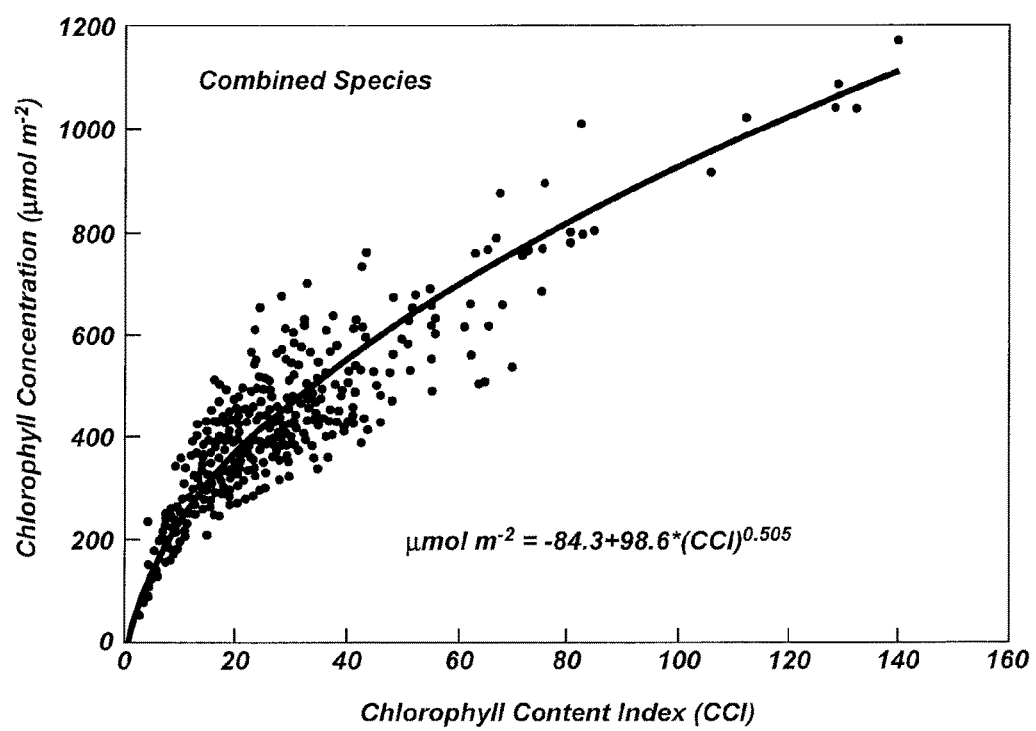

FIGS. 4A and 4B illustrate an optical/absolute relationship (lines 402-446) between CCI values and chlorophyll concentration ($\mu mol\ m^{-2}$) for 22 individual species. In particular, FIG. 4A shows the optical/absolute relationship for 22 individual species, and FIG. 4B shows the optical/absolute relationship (line 450) for all 22 individual species combined. The molar mass of the chlorophyll molecule is about 900 grams per mole. These measurements can be converted to mass per unit area.

Figure 5:
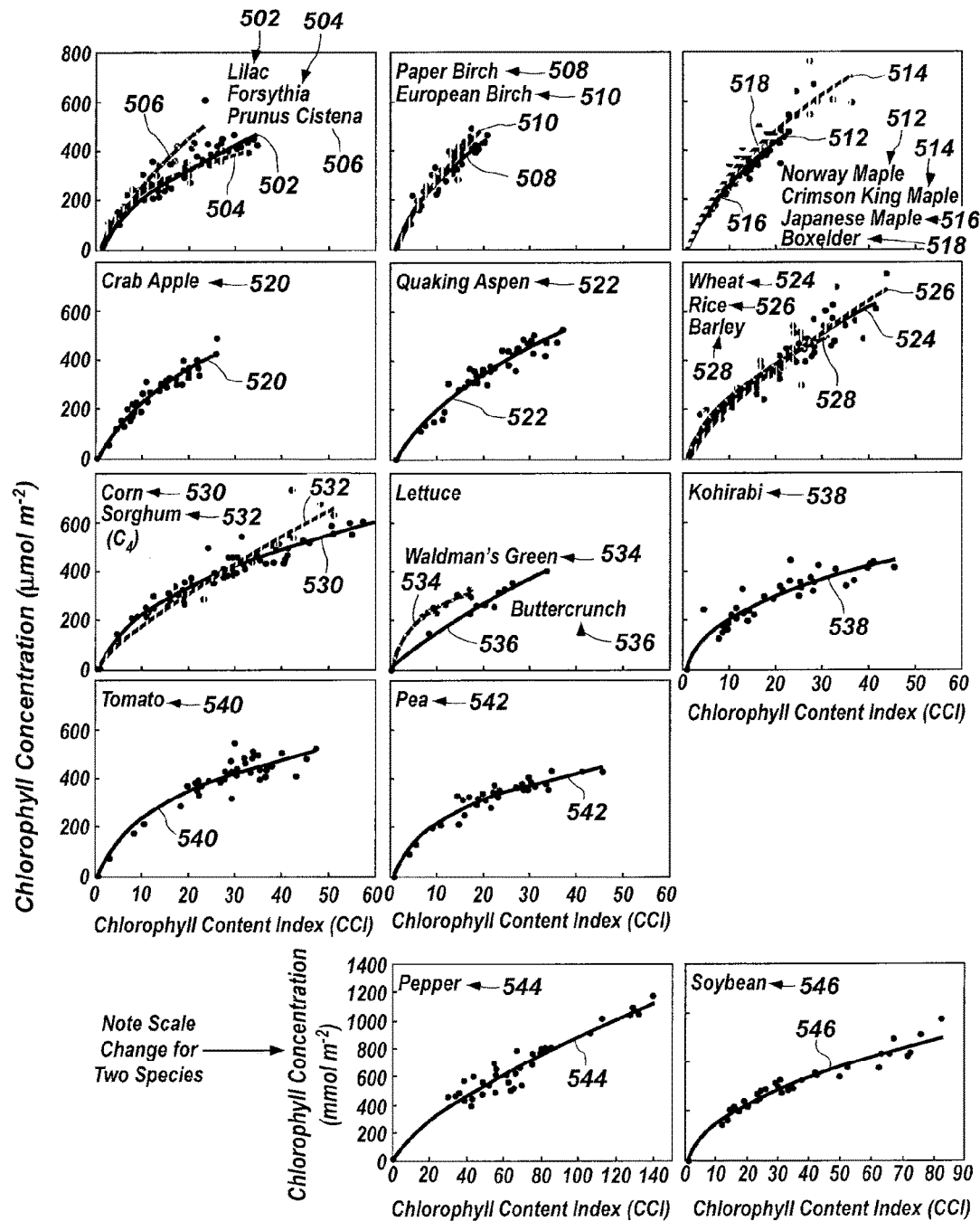
FIG. 5 shows the relationship between chlorophyll content index (CCI) and chlorophyll concentration (µmol $m^{-2}$) for 22 individual species.

The 22 individual species in the study for this disclosure had a wide range of optical/absolute chlorophyll relationships as seen in FIG. 4A. In addition to deriving a single universal relationship for all species (FIG. 4B), individual equations for each species were also derived (See Table 2; FIG. 5).

FIG. 5 shows optical/absolute relationships (lines 502-546) between CCI values and chlorophyll concentration ($\mu mol\ m^{-2}$) for 22 individual species. Equations for each relationship are provided in Table 2.

Although it appears that some cultivars within a species can be expressed by a single relationship, we found significantly different optical/absolute relationships between two lettuce cultivars (cv. Waldman's Green and cv. Buttercrunch; *Lactuca sativa*) (FIG. 5). However, our data indicate that the monocots barley, wheat, and rice have a similar optical/absolute chlorophyll concentration relationship (FIG. 5).

Uniformity of Replicate Meters

Figure 6A:
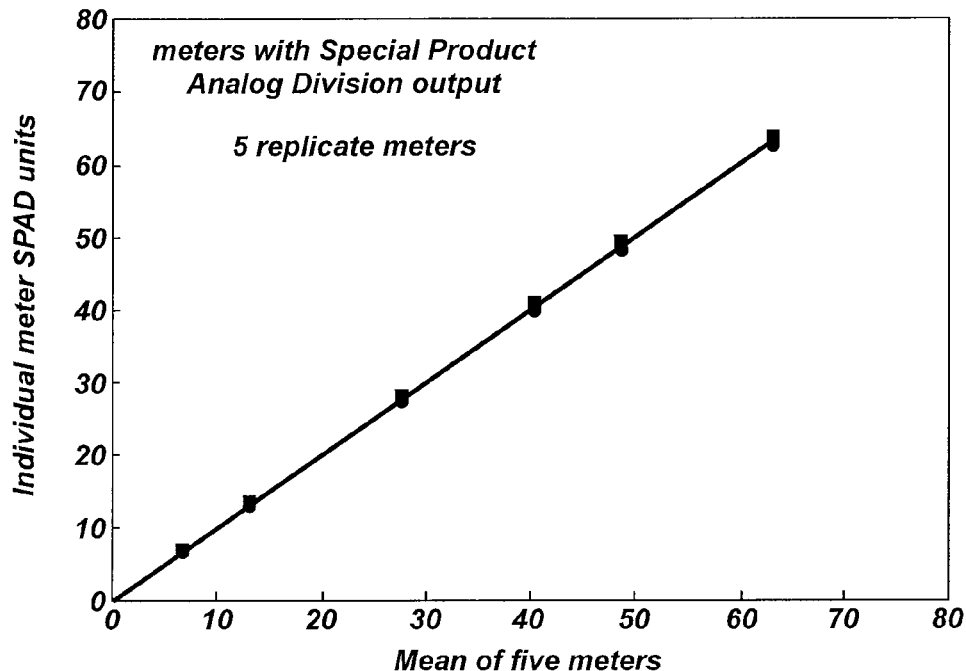
FIGS. 6A and 6B detail the uniformity of the two most common chlorophyll meters.
Figure 6B:
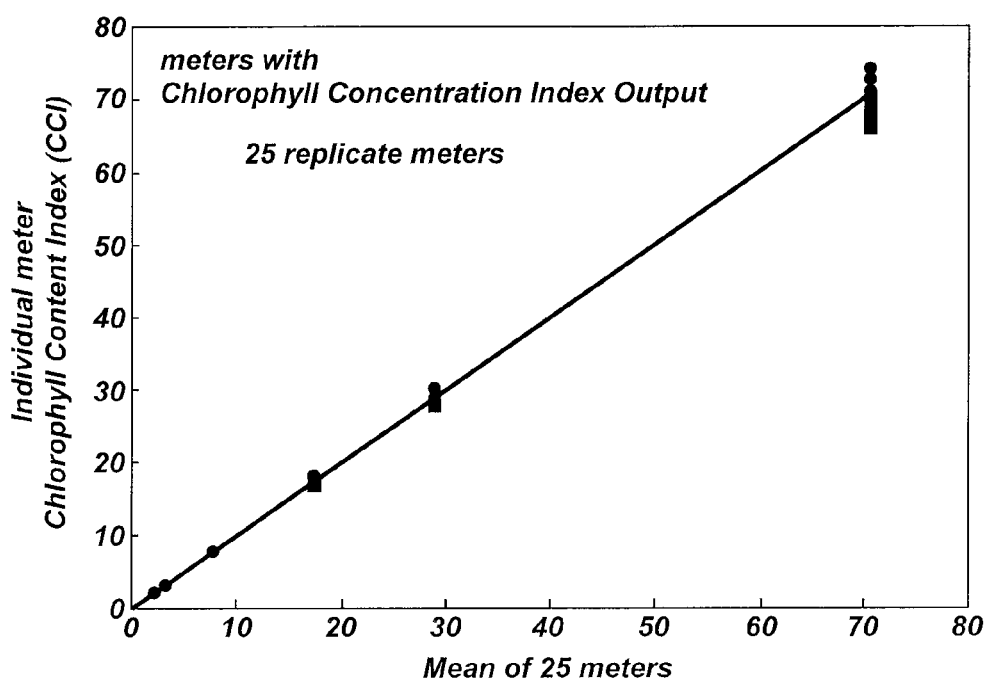

Output from each individual chlorophyll meter was plotted against the mean of all chlorophyll meters of the same type to determine variation among studies due to variation among replicate meters (FIGS. 6A and 6B). Mean coefficient of variation was 2.60% for the CCM-200 meter and 1.10% for the SPAD-502 meter.

FIG. 6A details the uniformity of the two most common chlorophyll meters. The output of individual chlorophyll meters was compared to the mean of all chlorophyll meters of the same type. Measurements were made on colored filters to provide a uniform reference. As shown by FIG. 6A, Five Minolta model SPAD-502 meters manufactured from 1992 to 2008 were evaluated. As shown in FIG. 6B, 25 Opti-Sciences model CCM-200 meters manufactured from 2007 to 2013 were evaluated. The Coefficient of Variation (standard deviation/mean) was 1.1% among meters with SPAD unit output, and 2.6% among meters with CCI output. Both types of meters were highly uniform and differences among meters are much smaller than differences in genetic, environmental, and extraction/analytical techniques.

Inter-Conversion Between Units

Figure 7A:
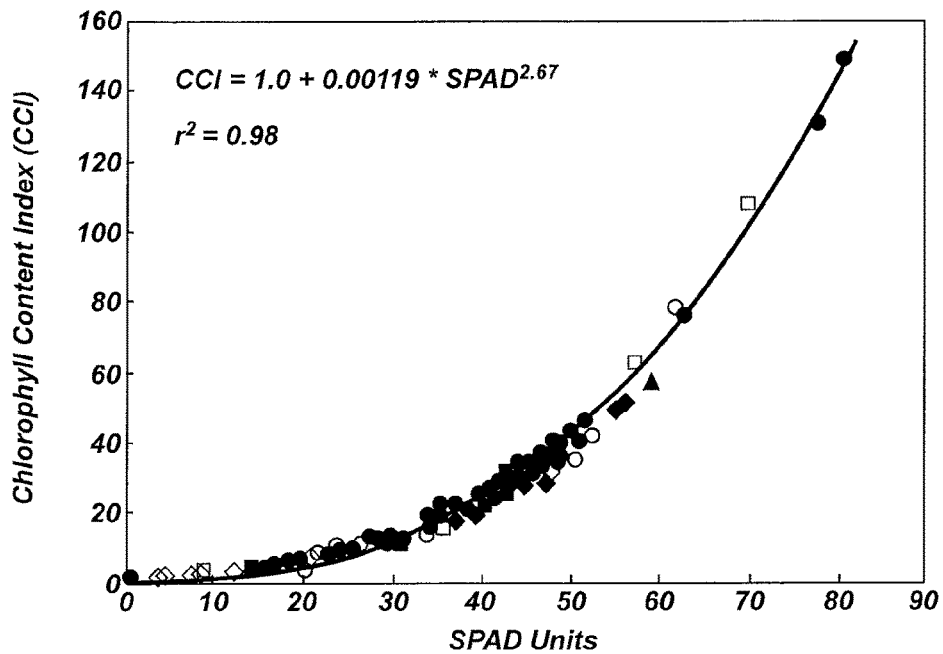
FIGS. 7A and 7B contain equations to convert (FIG. 7A) SPAD units to chlorophyll content index (CCI) and (FIG. 7B) CCI to SPAD units.
Figure 7B:
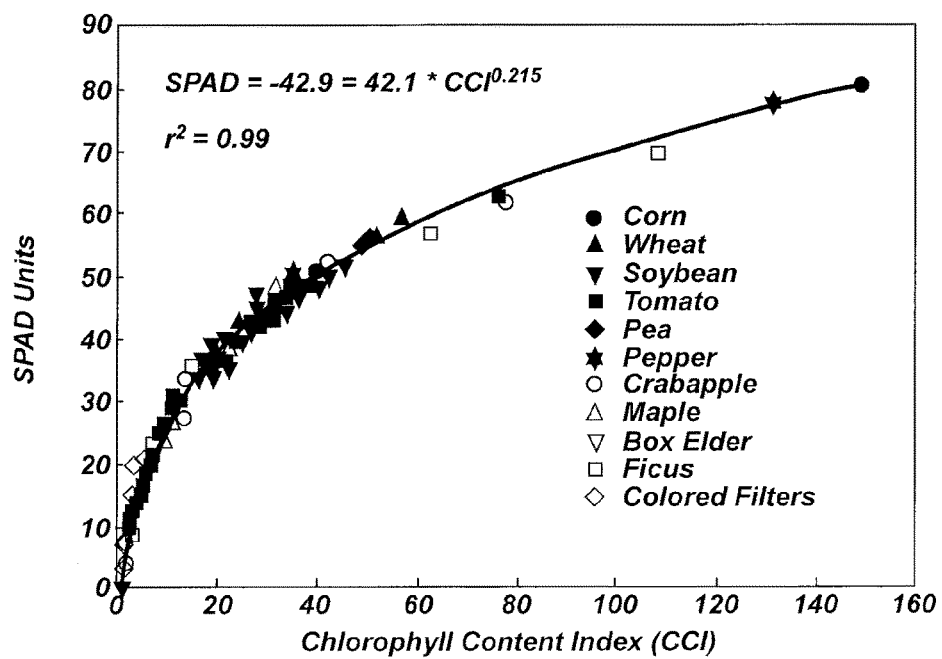

Our results indicate that that universal relationships can be used to inter-convert between CCI values and SPAD values (FIGS. 7A and 7B; $r^2$=0.98, 0.99). Inter-converting between CCI values and SPAD values may be useful for users who prefer one value over the other value, such as if the user has instructions they have developed based on one of the different types of values.

A relationship was developed by Richardson et al. (2002) for converting SPAD units to CCI units ($r^2$=0.97). However, the chlorophyll meter conversion relationship created by Richardson et al. (2002) was based on measurements on Paper Birch leaves with a narrow range of chlorophyll (SPAD units of zero to 40). It was also developed for a prototype CCM-200 meter, which had a different wavelength for the red absorption wavelength. This meter was replaced with the current version in late 2002. The chlorophyll meter conversion curves for this study were developed from multiple species over a wide range of chlorophyll concentrations.

FIGS. 7A and 7B contain equations to convert between SPAD values and CCI values. In particular FIG. 7A contains equations for converting from SPAD values to CCI values, and FIG. 7B contains equations for converting from CCI values to SPAD values. Data are from replicate measurements of multiple species. Each comparison measurement was made on the same spot on each leaf.

Monocot and Dicot Species Differences

Figure 8:
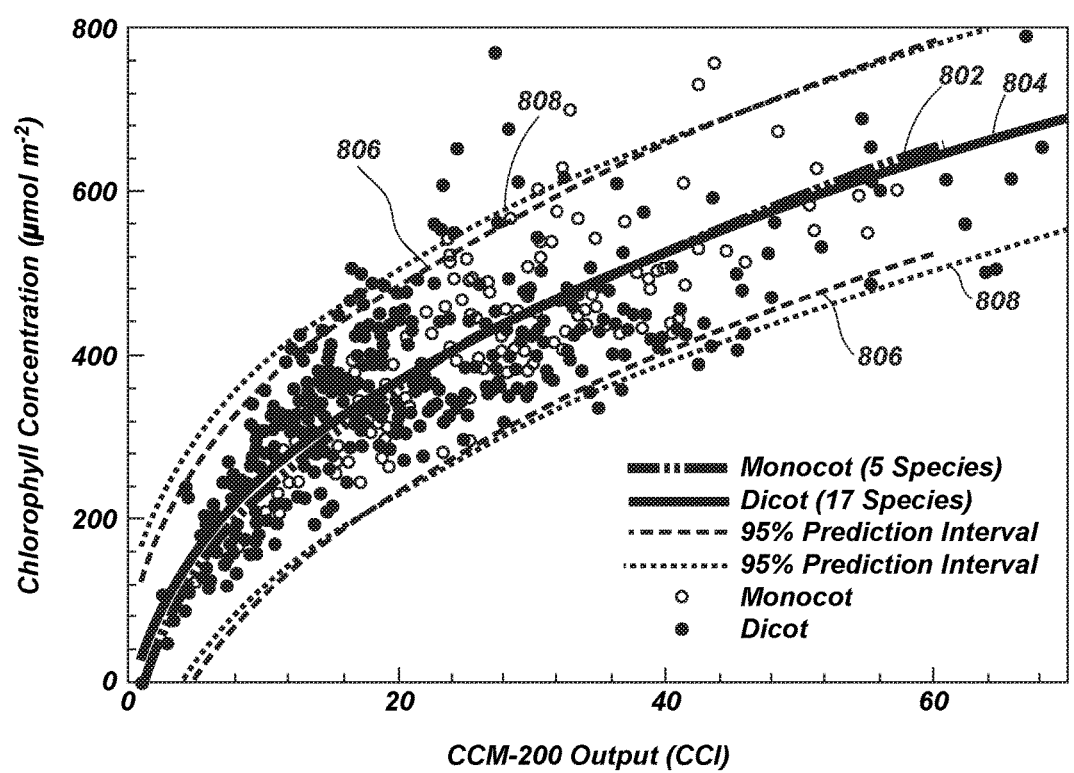
FIG. 8 illustrates the relationship between chlorophyll content index (CCI) and chlorophyll concentration (µmol $m^{-2}$) for the mean of five monocot species and 17 dicot species.

FIG. 8 illustrates the optical/absolute relationship (lines 802, 804) between CCI values and chlorophyll concentration ($\mu mol\ m^{-2}$) for the mean of five monocot species and 17 dicot species. As shown in FIG. 8, the absolute/optical relationships between CCI and chlorophyll concentration for the mean of five monocot species and the mean of 17 dicot species were not significantly different as indicated by the 95% prediction intervals (lines 806, 808).

Chlorophyll a/b Ratio

The mean chlorophyll a/b ratio for $C_3$ and $C_4$ plants was 3.2 and 6.3 respectively (Table 2). These results are similar to the values of Chang and Troughton (1972) when corrected for the underestimation of the Arnon (1949) equation ($C_3$: 3.9 and $C_4$: 5).

There was a small positive relationship between chlorophyll concentration and the a/b ratio. The coefficient of determination between absolute chlorophyll concentration and a/b ratio was 0.68 for Lilac, 0.48 for Japanese Maple and less than 0.20 for all other species (data not shown).

Relationship Between Transmission and Absolute Chlorophyll and Cell Wall Content of Leaves The output of both Minolta SPAD-502 and Opti-Sciences CCM-200 meters is based on the ratio of transmission of NIR to red wavelengths. Transmission of radiation is non-linearly related to the amount of absorbing compound in leaf tissue and linearly related to the absorbance of compound (Atkins, 1990). Absorbance is the negative log of transmittance.

Non-chlorophyll compounds (primarily cell walls) absorb radiation similarly at both red and NIR wavelengths, so transmission of red light is similarly affected by both compounds. Transmission of NIR radiation is not affected by chlorophyll and is thus primarily determined by the amount of non-chlorophyll compounds. Assuming a uniform distribution of chlorophyll in leaves, the absolute amount of cell wall and chlorophyll in leaves can be determined from the ratio of percent transmission by the following relationship based on the Beer-Lambert law:

$$CCI = \frac{\% \text{ Transmission } NIR}{\% \text{ Transmission } RED} \approx \frac{e^{-[cell\ wall]}}{e^{-[chlorophyll+cell\ wall]}} = \frac{e^{[chlorophyll+cell\ wall]}}{e^{[cell\ wall]}} \quad (6)$$

$$CCI = e^{[chlorophyll+cell\ wall]} - e^{[cell\ wall]} \quad (7)$$

$$\ln(CCI) = \ln(e^{[chlorophyll+cell\ wall]}) - \ln(e^{[cell\ wall]}) \quad (8)$$

$$\ln(CCI) = [chlorophyll+cell\ wall] - [cell\ wall] \quad (9)$$

$$SPAD \approx \ln(CCI) = [chlorophyll] \quad (10)$$

As shown in equation (10), if chlorophyll is uniformly distributed, SPAD values would be linearly related to chlorophyll concentration of leaves and CCI values would be related to chlorophyll concentration as a logarithmic function. Chlorophyll, however, is not uniformly distributed in leaves and this causes concentration estimates based on transmission measurements to deviate from the equations shown above. The optical changes caused by non-uniform distribution are caused by the sieve and detour effects.

The Sieve Effect and the Detour Effect

The transmission of light through a leaf is affected by pigment concentration and pigment spatial distribution in leaves. Non-uniform chlorophyll distribution (clumping of chlorophyll molecules) decreases transmission of light at lower chlorophyll concentrations and increases transmission of light at higher chlorophyll concentrations. Distribution of chlorophyll within a leaf is influenced by structural organization of grana within chloroplasts, chloroplasts within cells, and cells within tissue layers (Fukshansky, Vonremisowsky, Mcclendon, Ritterbusch, Richter and Mohr, 1993). When light passes through leaf tissue without encountering an absorber it is known as the sieve effect, which increases with increasing non-uniformity of chloroplasts. As chloroplast uniformity increases, efficiency of red light absorption increases.

The detour effect (light scattering) increases the optical path-length through the leaf, which reduces light transmission. The leaf reflectance at the reference NIR wavelength is much higher than the leaf reflectance at the red chlorophyll absorption wavelength. This causes the detour effect to be more pronounced for the reference NIR wavelength. The detour effect reduces transmission per unit chlorophyll (Monje and Bugbee 1992, Naus et al. 2010, Uddling et al. 2007). Differing optical/absolute chlorophyll relationships among species are likely due to different chlorophyll distribution patterns and thus differing sieve and detour effects.

The sieve effect causes transmission to increase and thus the optical chlorophyll measurement is lower than a sample with uniform chlorophyll distribution (Jifon et al., 2005, Marenco et al., 2009, Monje and Bugbee, 1992, Richardson et al., 2002, Uddling et al., 2007). The detour effect decreases transmission of light compared to a sample with uniform chlorophyll distribution and thus increases the optical chlorophyll measurement (Uddling et al., 2007). Uddling et al. (2007) observed a noticeable deviation caused by the sieve affect above a SPAD value of 20 and a relatively larger deviation caused by the detour effect below a SPAD value of 20. The combined effects of these relationships on the optical/absolute chlorophyll relationship cause a predictable deviation from the theoretical relationship (FIGS. 9A and 9B).

Figure 9A:
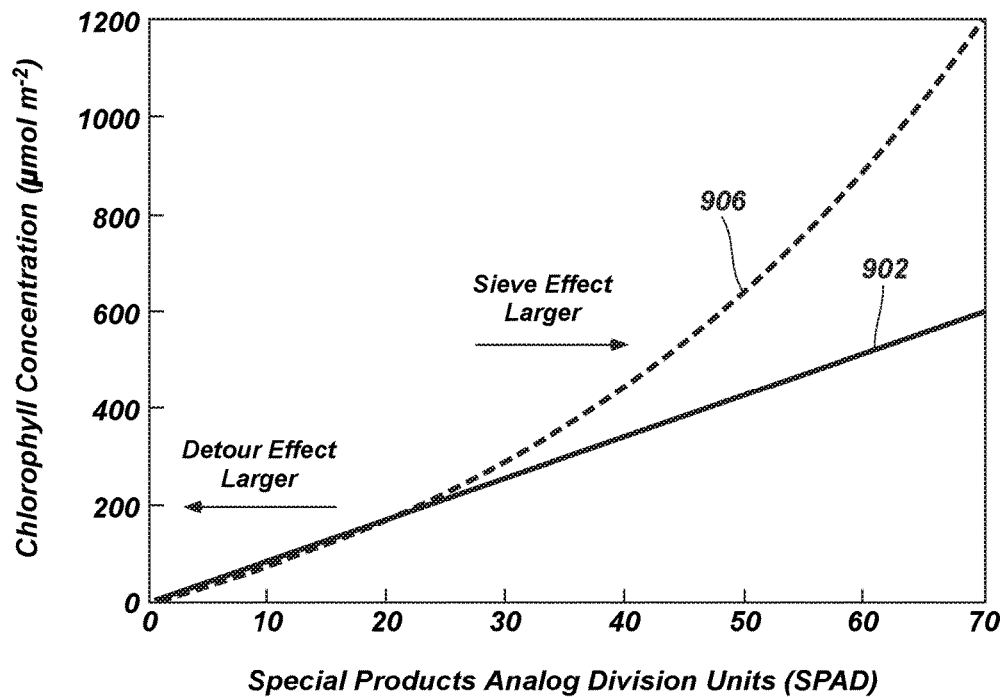
FIGS. 9A and 9B show the impact of the detour (light scattering) and sieve effects (non-uniform chlorophyll distribution) on the optical/absolute chlorophyll concentration relationship for (FIG. 9A) SPAD units and (FIG. 9B) chlorophyll content index (CCI).
Figure 9B:
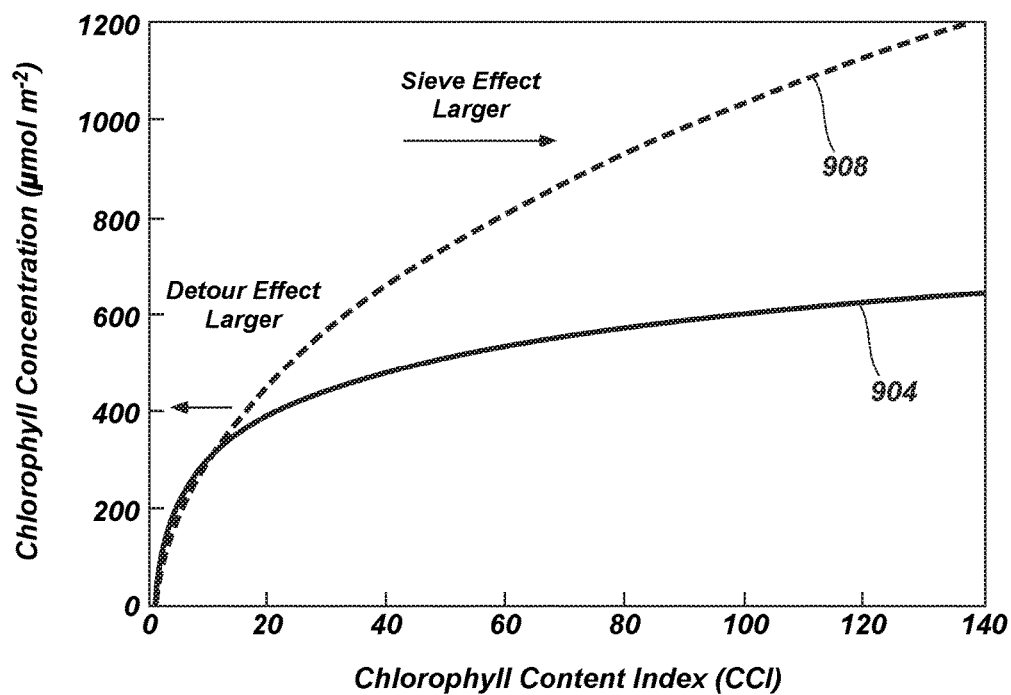

FIGS. 9A and 9B show the impact of the detour (light scattering) and sieve effects (non-uniform chlorophyll distribution) on the optical/absolute chlorophyll concentration relationship for SPAD values (FIG. 9A) and CCI values (FIG. 9B). Lines 902, 904 indicate the theoretical relationship if chlorophyll was uniformly distributed in the leaf, whereas lines 906, 908 result from the measured data of FIG. 1. Thus, the sieve effect tended to be larger as chlorophyll content increased for both SPAD values and CCI values, and the detour effect tended to be larger as chlorophyll content decreased.

Environmental Effects on Optical Measurements

Changes in leaf environment have the potential to alter leaf morphology, leaf thickness, and chloroplast distribution. Changes in specific leaf area, often caused by water or temperature stress, have the potential to alter the optical/absolute chlorophyll relationship. Light scatter is higher in thicker leaves (Naus et al., 2010); however, unlike other studies (Campbell, Mobley, Marini and Pfeiffer, 1990, Jifon et al., 2005), we did not find a different optical/absolute chlorophyll relationship between leaves of the same species (tomatoes, peppers, maize, peas) grown in greenhouse vs. outdoor environments. Our data for Paper Birch leaves match the corrected data of Richardson et al. (2002), in spite of measurements made on seedlings in a greenhouse (Richardson et al., 2002) and our measurements on mature trees in an arid environment in Utah. Collectively, these findings do not suggest a significant environmental effect on the optical/absolute chlorophyll concentration relationship.

Light-Dependent Chloroplast Movement

Light intensity can alter chloroplast orientation (Hoel and Solhaug, 1998, Naus et al., 2010), which can affect the optical/absolute chlorophyll relationship. Davis et al. (2011) found that the effects of chloroplast movement were greatest in shade species and found that mean maximum percent change in red light transmission between low and high light acclimation was 6.3% (Stdev 4.7%) for shade-grown leaves and 2.1% (Stdev 1.6%) for sun-grown leaves. This change in chloroplast orientation in response to light is small, but potentially significant in the optical/absolute chlorophyll relationship.

Davis et al. (2011) hypothesized that the amount of chlorophyll movement was correlated with cell diameter. Narrower, more columnar cells of sun leaves may have a greater restriction on chloroplast movement than shade leaf cells. Leaf cell size and shape differ greatly with species (Lee, Oberbauer, Johnson, Krishnapilay, Mansor, Mohamad and Yap, 2000), which may explain varying degrees of chloroplast movement among species. All measurements in this study were made in high light to minimize effects from light dependent chloroplast movement.

Differences Among Replicate Meters

Previous studies on differences among meters have not provided a comprehensive test of meter variability (Markwell et al., 1995; Marquard and Tipton, 1987). Our results indicate that differences among replicate meters were minimal, suggesting differences among studies in the optical/absolute chlorophyll concentration relationship are not caused by different meters.

Most of the variability among optical/absolute chlorophyll concentration relationships of similar species is likely due to the variability of extraction methods, extraction solvents, chlorophyll concentration equations, and the resolution of spectrophotometers. Some studies have determined chlorophyll concentration using diode array spectrophotometers with methanol extinction coefficients from Porra (1989) (e.g., Cerovic et al. 2012). This is contrary to the recommendations of Wellburn (1994) and would likely lead to errors in determination of absolute chlorophyll concentration. Porra et al. (1989) used a Hitachi 3200 spectrophotometer with a spectral resolution of 0.1-0.5 nm over the visible spectrum for extract extinction coefficient determination. Spectrophotometers with similar resolution should be used for best accuracy.

Differences Among Cultivars of the Same Species

Many studies have shown that cultivars within species have similar optical/absolute chlorophyll concentration relationships, but this is not always the case. There were significant differences in the optical/absolute chlorophyll relationship for the two lettuce cultivars in this study. This difference can most likely be attributed to the difference in leaf morphology and anatomy in these two cultivars.

Relationship Between Monocots and Dicots

On the basis of measurements in two monocot and two dicot species, Cerovic et al. (2012) suggested that there may be a difference between monocots and dicots.

However, no significant difference was found between monocot and dicot curves for the five monocot and 17 dicot species in this study (FIG. 8). In spite of anatomical differences, it does not appear that monocot and dicot species have different optical/absolute chlorophyll concentration relationships.

Chlorophyll a/b Ratio

Chlorophyll a/b ratios are often reported to be a 3 to 1 ratio, but this ratio has not been widely studied. Chang and Troughton (1972) reported typical ratios of C3 plants as 3 to 1; and ratios in C4 plants as 5 to 1. They suggest that the a/b ratio is affected by both genetics and by biotic and abiotic factors. We found a similar difference in the ratios for C3 and C4 plants (Table 2). We did not find a difference in the optical/absolute chlorophyll relationship between C4 and C3 plants in spite of the anatomical difference between these plant groups, and a significant difference in the chlorophyll a/b ratio.

The Slope of the Optical/Absolute Relationship Indicates Differences in Chlorophyll Distribution and Radiation Capture Species with a steep slope in the optical/absolute relationship poorly intercept light per unit chlorophyll; species with a low slope efficiently intercept light per unit chlorophyll. It is likely that increasing non-uniformity of chlorophyll leads to a steeper slope of this relationship. This study highlights the enormous differences in chlorophyll distribution among species and even within species. The lettuce cultivar (Buttercrunch) had one of the lowest slopes and the other (Waldman's Green) had one of the highest slopes.

Chlorophyll Meter and Related Methods

Figure 10:
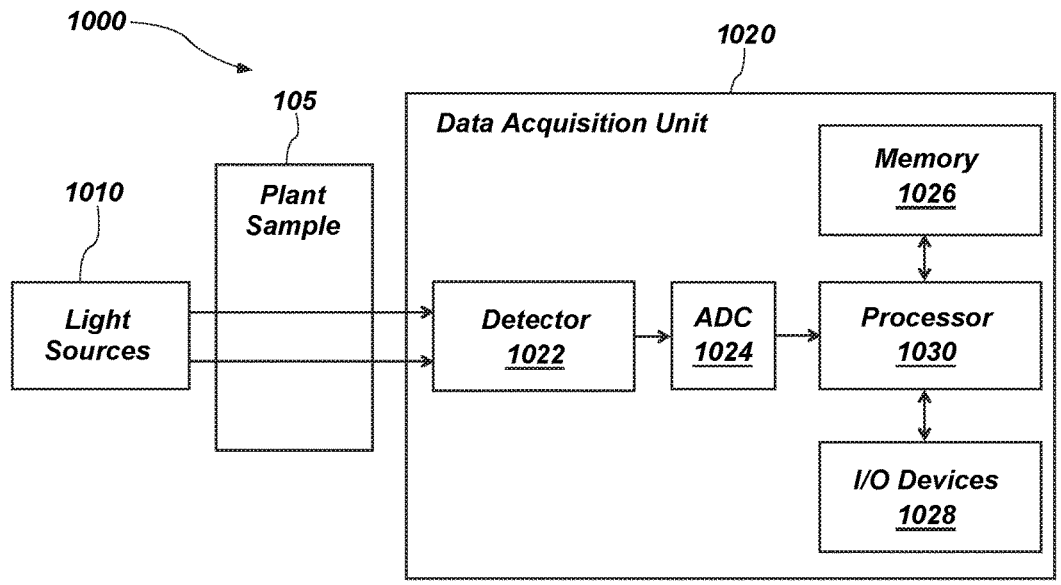
FIG. 10 is a simplified schematic diagram of a chlorophyll meter according to an embodiment of the disclosure.

FIG. 10 is a simplified schematic diagram of a chlorophyll meter 1000 according to an embodiment of the disclosure. The chlorophyll meter 1000 may include a plurality of light sources 1010 and a data acquisition unit 1020. The data acquisition unit 1020 may include a detector 1022, an analog-to-digital converter (ADC) 1024, memory 1026, and input/output (I/O) devices 1028 that are operably coupled with a processor 1030. The processor 1030 may also be operably coupled with the light sources 1010. In some embodiments, the chlorophyll meter 1000 may be a portable handheld device, with each component being part of the same assembly.

Memory 1026 may be a computer-readable medium that includes volatile memory and/or non-volatile memory for storing instructions for execution by the processor 1030, temporarily storing information during operation, long-term data storage (e.g., storage of chlorophyll data measurements), and combinations thereof.

The light sources 1010 may include a plurality of light emitting diodes (LEDs) that emit light for transmission through a plant sample 105 at different wavelengths. A first light source may emit light at a first wavelength, such as red radiation (e.g., approximately 650 nm) and a second light source may emit light at a second wavelength, such as near infrared (NIR) (e.g., approximately 900 nm). In some embodiments, the first light source may be centered at 653 nm and the second light source may be centered at 931 nm. In some embodiments, the detector 1022 may include a plurality of detectors to measure the amount of light transmitted through the plant sample 105. A first detector may be paired with the first light source, and a second detector may be paired with the second light source.

The I/O devices 1028 may include input devices (e.g., keypad, touchscreen, buttons, etc.) for receiving inputs from a user or other sources. In some embodiments, the input devices may include a GPS device that is configured to receive GPS information to determine GPS coordinate that may be saved with each measurement. The I/O devices 1028 may also include output devices (e.g., electronic display, speaker, etc.) for conveying information to the user or to other devices. For example, the output devices may include an output port (e.g., USB port, RS-232, Ethernet, wireless transmitters, etc.) and other communication devices configured to provide data transfer to external devices (e.g., data download to an external computer). The chlorophyll meter 1000 may include additional components (e.g., such as amplifiers, mirrors, lenses, etc.) that are not shown for simplicity, but which may facilitate transmission of the light, reception of the light, and transmission of information within the chlorophyll meter 1000.

The processor 1030 may be configured to generate a chlorophyll content output responsive to an optical/absolute relationship that is determined by a matched combination of extraction method, extraction solvent, spectrophotometric equation, and spectrophotometer resolution to provide a plurality of different optical/absolute relationships among different species. Each of the optical/absolute relationships may be defined by an equation's chlorophyll concentration that is selectable by the user depending on which plant sample 105 is being tested. For example, the equations may be selected from the group consisting of those listed in Table 2 shown below. The equations may correspond to a plurality of different species. The chlorophyll meter 1000 may be configured to receive an input from the user indicating which plant sample 105 is being tested. In response to receiving the input, the processor 1030 may employ the corresponding equation as the optical/absolute relationship for determining the chlorophyll concentration to be displayed by the chlorophyll meter. While Table 2 shows equations for 23 different species, other equations for additional species are also contemplated. For example, additional equations may be developed for other species using the methods described herein. In some embodiments, a generic equation may be selected that was derived from the data from the other species, and the generic equation may be desirable if an individual equation is not available for a particular species to be measured.

In some embodiments, the user may desire to test a plant sample that is not available as an option on the user's chlorophyll meter 1000 at that time. In other words, the chlorophyll meter 1000 may not have a specific equation for a particular species that the user desires to measure. The chlorophyll meter 1000 may be configured to receive an input from the user to create an equation that may be stored in memory 1026 for future use. For example, the user may develop their own coefficients for an equation based on absolute chlorophyll measurements the user has made. The chlorophyll meter 1000 may request the coefficients to be input by the user, after which the chlorophyll meter 1000 may generate the optical/absolute relationship to be stored in memory for the new species. During subsequent use, the new species may be presented as an option to be selected by the user.

In operation, the user may select the particular type of plant sample being tested for the processor 1030 to know which equations to apply. The user may place the plant sample 105 between the light sources 1010 and the detector 1022 and initiate the sampling process, which causes the light sources 1010 to emit light to pass through the plant sample 105 at different wavelengths for a sample time (e.g., 3 seconds or less). The detector 1022 may detect the light from the first light source and the second light source transmitted through the plant sample 105, generate a first data signal indicative of the light transmitted through the plant sample 105 at the first wavelength, and generate a second data signal indicative of the light transmitted through the plant sample 105 at the second wavelength. These values may be used to determine the CCI values for the equation selected for the optical/absolute relationship for estimating chlorophyll content by the chlorophyll meter 1000. For example, the processor 1030 may compare the amount of light received by the detector 1022 with the amount of light emitted by the light sources 1010 to determine a transmittance of the light through the plant sample 105. That ratio may be applied to the appropriate equation to determine the chlorophyll content value to be output by the chlorophyll meter 1000.

The chlorophyll meter 1000 may display an output that shows the actual chlorophyll content (e.g., in units of $\mu$mol $m^{-2}$, mg $m^{-2}$, etc.) that results from the optical/absolute relationships being applied to the raw data. The chlorophyll meter 1000 may also display the underlying SPAD values and/or the CCI values as well. Displaying these values may be useful for users who are already comfortable with this data, and may have instructions and data correlated to those values based on their own experience and/or literature that have studied those values. As a result, the chlorophyll meter 1000 may be backwards compatible with data that users may be familiar with. The chlorophyll meter 1000 may be configured to display these values simultaneously with each other. In some embodiments, the chlorophyll meter 1000 may be configured to enable the user to switch between the chlorophyll concentration value, the SPAD value, and the CCI value being displayed on its electronic display.

In some embodiments, there may be different test types including a single measurement without any averaging, a multi-point average value, and a multi-point standard deviation value. The user may select the desired test type. The single measurement test may save every data point individually to the data file. The multi-point average test may record an average value for multiple measurements. In some embodiments, the user may also select the desired number of points of measurement to average (e.g., between 2 samples and 30 samples). The multi-point standard deviation test may record a standard deviation from the samples. Outliers may be automatically identified and eliminated when determining the standard deviation. In some embodiments, the individual data points used to obtain the average value or standard deviation may also be saved in the underlying data file.

Figure 11:
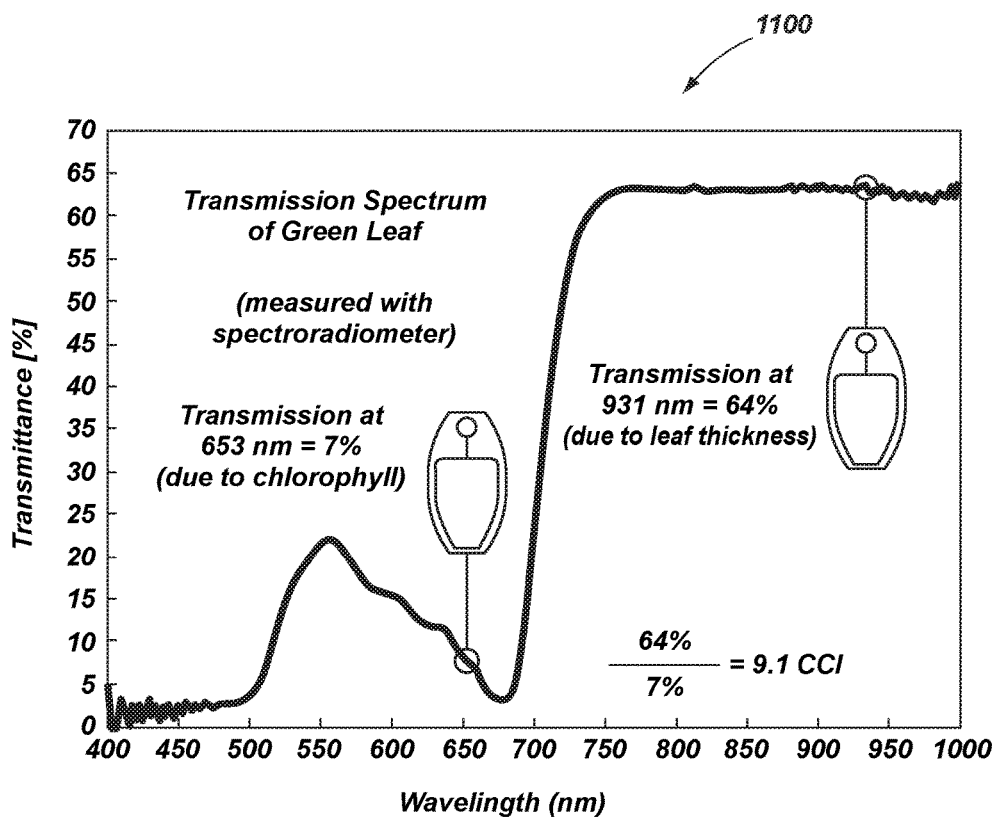
FIG. 11 is a plot showing a transmission spectrum of a plant sample for various wavelengths of light.

FIG. 11 is a plot 1100 showing a transmission spectrum of a plant sample for various wavelengths of light. Chlorophyll has distinct radiation absorption characteristics and is a strong absorber of photosynthetically active wavelengths (e.g., approximately 400 nm to 700 nm). Chlorophyll absorbs substantially less radiation at wavelengths greater than about 700 nm.

As shown in FIG. 11, the percentage of transmission may vary depending on the wavelength of light passing through the plant sample. For example, the percentage of transmittance may be approximately 7% for a wavelength of 653 nm, and the percentage of transmittance may be approximately 64% for a wavelength of 931 nm. These values are shown as an example, and may depend on chlorophyll content, sample thickness, species, and other factors. From these values, a ratio (e.g., CCI value) may be obtained based on the reference wavelength and the other transmitted wavelength. In some embodiments, other wavelengths may also be used to obtain an initial value for the ratio of transmittance between the reference wavelength and the other transmitted wavelength.

Figure 12:
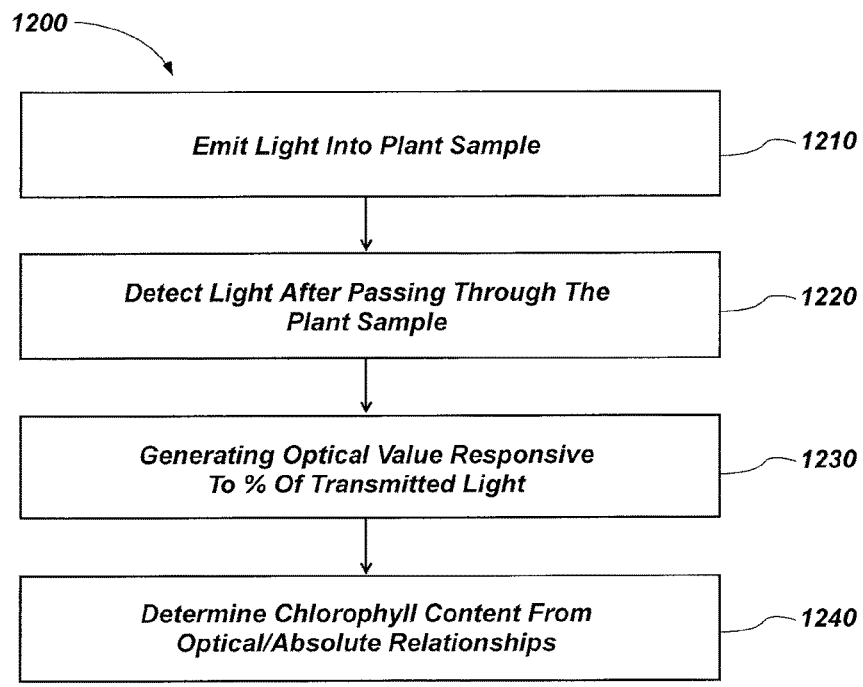
FIG. 12 is a flow chart illustrating a method for determining chlorophyll content of a plant sample.

FIG. 12 is a flow chart 1200 illustrating a method for determining chlorophyll content of a plant sample. At operation 1210, a plurality of light sources may emit light at a first wavelength and a second wavelength into a plant sample. The first wavelength and the second wavelength may be near infrared (NIR) (e.g., approximately 900 nm) and red (e.g., approximately 650 nm), respectively. At operation 1220, the light after passing through the plant sample may be detected. At operation 1230, an optical value (e.g., SPAD value, CCI value, etc.) may be generated responsive to a ratio of the % transmitted light through the plant sample for the first wavelength and the second wavelength. At operation 1240, chlorophyll content is determined based on the optical value compared with an optical/absolute chlorophyll relationship that was determined by a matched combination of extraction method, extraction solvent, spectrophotometric equation, and spectrophotometer resolution. The optical/absolute relationship may one of a plurality of different optical/absolute relationships that the user may select from for different species. Thus, the optical/absolute relationships used within the chlorophyll meter may be provide a variable, non-linear response for different plant samples that may be tested.

Table 2 lists a plurality of equations for determining chlorophyll concentration ($\mu$mol $m^{-2}$) from chlorophyll content index (CCI), $r^2$ values for each equation, and mean chlorophyll a/b ratio for 22 different species. The species are listed in order of increasing slope of the optical/absolute chlorophyll relationship. The mean chlorophyll a/b ratio was not correlated with the optical/absolute chlorophyll relationship. The two species (maize and sorghum) with C4 photosynthesis had the highest chlorophyll a/b ratio.

TABLE 2

| | Chlorophyll Concentration Equation ($\mu$mol m$^{-2}$) from CCI | $r^2$ | Mean Chlorophyll a/b ratio | Standard Deviation of a/b ratio |
|---|---|---|---|---|
| Deciduous Species | | | | |
| European Birch | $-76 + 85*(CCI)^{0.64}$ | 0.89 | 3.3 | 0.5 |
| Lilac | $-98 + 93*(CCI)^{0.51}$ | 0.95 | 2.6 | 0.5 |
| Norway Maple | $-95 + 96*(CCI)^{0.57}$ | 0.94 | 3.9 | 0.7 |
| Quaking Aspen | $-128 + 106*(CCI)^{0.50}$ | 0.92 | 3.3 | 0.3 |
| Purple Leaf Sand Cherry | $-144 + 113*(CCI)^{0.55}$ | 0.96 | 2.5 | 0.7 |
| Crab Apple | $-124 + 117*(CCI)^{0.47}$ | 0.93 | 4.4 | 1.4 |
| Paper Birch | $-120 + 135*(CCI)^{0.48}$ | 0.94 | 2.5 | 0.4 |
| Crimson King Maple | $-160 + 144*(CCI)^{0.50}$ | 0.90 | 2.6 | 0.3 |
| Japanese Maple | $-150 + 150*(CCI)^{0.43}$ | 0.97 | 1.9 | 0.1 |
| Box Elder | $-191 + 182*(CCI)^{0.38}$ | 0.92 | 2.7 | 0.3 |
| Forsythia | $-486 + 477*(CCI)^{0.18}$ | 0.93 | 2.6 | 0.5 |
| Annual Crop Plants | | | | |
| Sorghum (C$_4$) | $-8 + 29*(CCI)^{0.80}$ | 0.90 | 6.9 | 2.0 |
| Pepper | $-19 + 39*(CCI)^{0.69}$ | 0.92 | 3.7 | 0.7 |
| Rice | $-64 + 57*(CCI)^{0.68}$ | 0.82 | 5.0 | 1.5 |
| Wheat | $-84 + 79*(CCI)^{0.60}$ | 0.87 | 4.3 | 0.4 |
| Soybean | $-103 + 123*(CCI)^{0.47}$ | 0.95 | 4.2 | 0.6 |
| Maize (C$_4$) | $-121 + 129*(CCI)^{0.42}$ | 0.84 | 5.7 | 1.4 |
| Barley | $-132 + 146*(CCI)^{0.43}$ | 0.95 | 3.1 | 0.7 |
| Kohlrabi | $-150 + 162*(CCI)^{0.34}$ | 0.83 | 3.1 | 0.8 |
| Tomato | $-328 + 304*(CCI)^{0.26}$ | 0.87 | 2.9 | 0.7 |
| Pea | $-334 + 316*(CCI)^{0.24}$ | 0.84 | 3.8 | 0.9 |
| Lettuce | | | | |
| Waldman's Green | $-2204 + 2204*(CCI)^{0.04}$ | 0.98 | 2.7 | 0.2 |
| Buttercrunch | $-29 + 32*(CCI)^{0.74}$ | 0.98 | 2.5 | 0.2 |

Each of the equations of Table 2 may be implemented for defining the optical/absolute relationship of the chlorophyll meter 1000 (FIG. 10) and the method 1200 (FIG. 12) for determining chlorophyll content. Therefore, embodiments of the disclosure include a plurality of relationships between optical transmission ratios and absolute chlorophyll concentration that provide a non-uniform distribution among species for a variable, non-linear response. These relationships more rigorously link in situ optical measurements with in vitro chlorophyll concentration and provide insight to strategies for single-leaf radiation capture among diverse species. The "CCI" variable may be one of the various CCI values described above.

Figure 13:
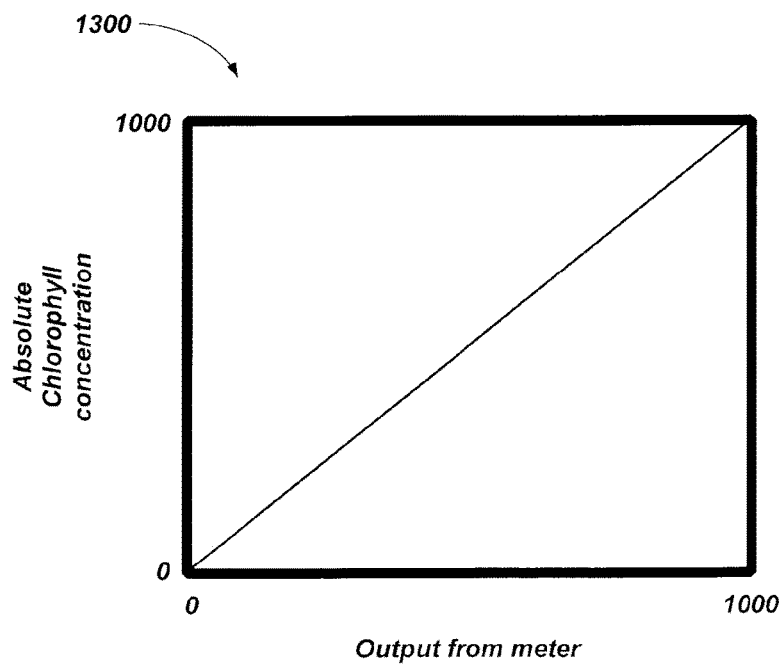
FIG. 13 is a plot showing an output from the chlorophyll meter plotted against an absolute chlorophyll concentration.

FIG. 13 is a plot 1300 showing an output from the chlorophyll meter plotted against an absolute chlorophyll concentration. The output from the chlorophyll meter may be the optical output that is in units of chlorophyll content rather than using the SPAD and CCI values that are not in units of chlorophyll concentration. As shown in FIG. 13, the chlorophyll meter may be configured to linearize the data and output the chlorophyll concentration of a plant sample with units of amount of chlorophyll (typically either moles, or grams), per unit area of leaf. For example, micromoles per square meter ($\mu$mol m$^{-2}$), mass per area of leaf surface, and milligrams per square meter (mg m$^{-2}$), may be used to describe chlorophyll concentration. While the optical/absolute relationships themselves may be non-linear (see FIGS. 4A and 4B), the output displayed by the chlorophyll meter may be linearly related to the absolute chlorophyll concentration values that may be measured through non-optical methods. The linear nature of the output may be within a tolerance range (e.g., ±1%) for a resolution (e.g., ±10 $\mu$mol m$^{-2}$) of the chlorophyll meter.

Figure 14:
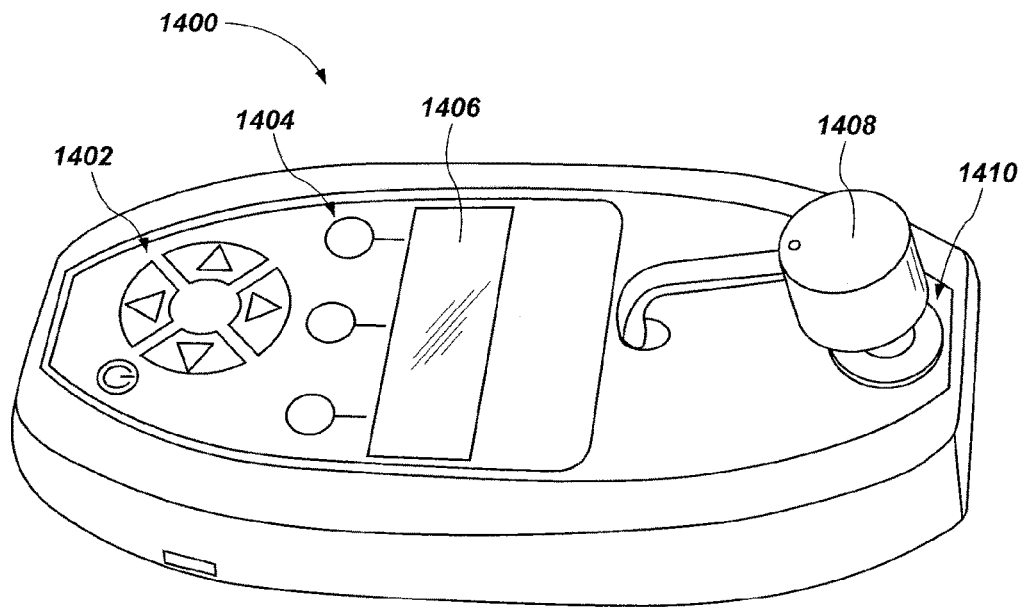
FIG. 14 is a perspective side view of a chlorophyll meter according to an embodiment of the disclosure.

FIG. 14 is a perspective side view of a chlorophyll meter 1400 according to an embodiment of the disclosure. The chlorophyll meter includes an external housing for the components discussed above with respect to FIG. 10. The chlorophyll meter 1400 includes navigation buttons 1402 for navigating through menu options on the electronic display 1406. Selection buttons 1404 may be used to select the menu options presented. In some embodiments, other form of input/output devices may be used, such as a touch screen display that performs both input and output functions. The chlorophyll meter 1400 may also include a sampling head 1408 that aligns with a detector region 1410. The sampling head 1408 contains the light sources (FIG. 10) that are used to emit the light through the plant sample that is inserted in the detector region 1410 (also referred to as a "sample chamber").

Figure 15:
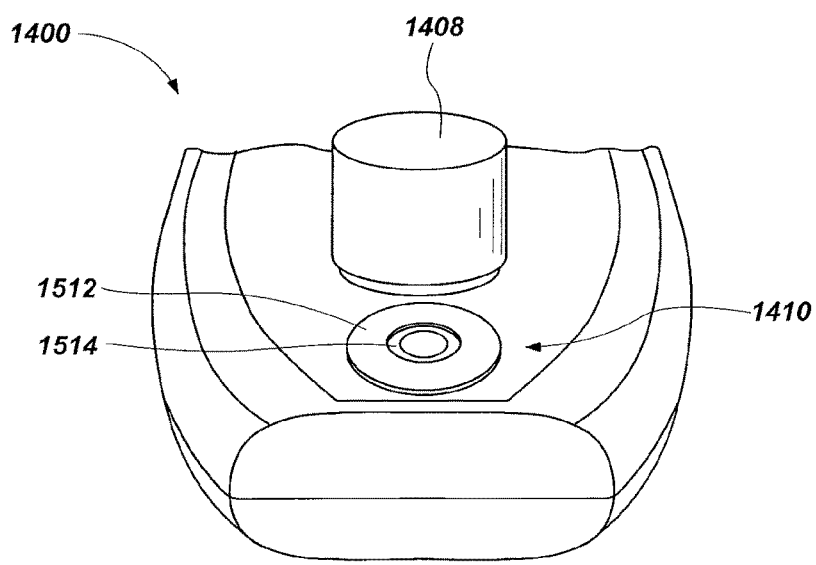
FIG. 15 is a perspective front view of the chlorophyll meter of FIG. 14.

FIG. 15 is a perspective front view of the chlorophyll meter 1400 of FIG. 14. The detector region 1410 may include a foam insert 1512 and field of view reducer 1514. The foam insert 1512 may abut a corresponding foam insert on the sampling head 1408 to provide a cushioning effect when the sampling head 1408 is moved into its sampling position. The foam insert 1512 may also define an outer field of view for the detector region 1410. The field of view reducer 1514 may be a ring that removably fits within the foam insert 1512 to cause the field of view for the detector region 1410 to be reduced. Thus, the field of view may be reduced or increased as desired. As an example, the field of view may be 63.6 mm$^2$ with the field of view reducer 1514 removed, and 19.6 mm$^2$ with the field of view reducer 1514 inserted—resulting in approximately 30% reduction from the larger size. Of course, other areas are contemplated. In addition, multiple field of view reducers 1514 may be used to provide additional reductions for more than two different possible areas. Reducing the field of view may permit different sizes of plant samples to be measured.

Although the foregoing description contains many specifics, these are not to be construed as limiting the scope of the disclosure, but merely as providing certain exemplary embodiments. Similarly, other embodiments of the disclosure may be devised which do not depart from the scope of the disclosure. For example, features described herein with reference to one embodiment also may be provided in others of the embodiments described herein. The scope of the claimed invention is, therefore, indicated and limited only by the appended claims and their legal equivalents, rather than by the foregoing description.

What is claimed is:

1. A chlorophyll meter, comprising:
   a first light source configured to emit light having a first wavelength;
   a second light source configured to emit light having a second wavelength;
   a detector configured to:
      detect the light from the first light source and the second light source transmitted through a plant sample;
      generate a first data signal indicative of the light transmitted through the plant sample at the first wavelength; and generate a second data signal indicative of the light transmitted through the plant sample at the second wavelength; and a processor operably coupled with the first light source, the second light source, and the detector, wherein the processor is configured to generate a chlorophyll content output responsive to an optical/absolute relationship defined by an equation selected from the group consisting of chlorophyll concentration being equal to:

about $-76+85*(CCI)^{0.64}$;
about $-98+93*(CCI)^{0.51}$;
about $-95+96*(CCI)^{0.57}$;
about $-128+106*(CCI)^{0.50}$;
about $-144+113*(CCI)^{0.55}$;
about $-124+117*(CCI)^{0.47}$;
about $-120+135*(CCI)^{0.48}$;
about $-160+144*(CCI)^{0.50}$;
about $-150+150*(CCI)^{0.43}$;
about $-191+182*(CCI)^{0.38}$; and
about $-486+477*(CCI)^{0.18}$, wherein $$CCI = \frac{\% \text{ Transmission first wavelength}}{\% \text{ Transmission second wavelength}}.$$

2. The chlorophyll meter of claim 1, wherein the equation for chlorophyll concentration being equal to:
about $-76+85*(CCI)^{0.64}$ is for European Birch;
about $-98+93*(CCI)^{0.51}$ is for Lilac;
about $-95+96*(CCI)^{0.57}$ is for Norway Maple;
about $-128+106*(CCI)^{0.50}$ is for Quaking Aspen;
about $-144+113*(CCI)^{0.55}$ is for Purple Leaf Sand Cherry;
about $-124+117*(CCI)^{0.47}$ is for Crab Apple;
about $-120+135*(CCI)^{0.48}$ is for Paper Birch;
about $-160+144*(CCI)^{0.50}$ is for Crimson King Maple;
about $-150+150*(CCI)^{0.43}$ is for Japanese Maple;
about $-191+182*(CCI)^{0.38}$ is for Box Elder; and
about $-486+477*(CCI)^{0.18}$ is for Forsythia.

3. The chlorophyll meter of claim 2, wherein $$CCI = \frac{\% \text{ Transmission 940 nm}}{\% \text{ Transmission 650 nm}}.$$

4. The chlorophyll meter of claim 2, wherein $$CCI = \frac{\% \text{ Transmission 931 nm}}{\% \text{ Transmission 653 nm}}.$$

5. The chlorophyll meter of claim 1, wherein $$CCI = \frac{\% \text{ Transmission } NIR}{\% \text{ Transmission } RED}.$$

6. The chlorophyll meter of claim 1, wherein the first wavelength is approximately 900 nm, and the second wavelength is approximately 650 nm.

7. A chlorophyll meter, comprising:
a first light source configured to emit light having a first wavelength;
a second light source configured to emit light having a second wavelength;
a detector configured to:
detect the light from the first light source and the second light source transmitted through a plant sample;
generate a first data signal indicative of the light transmitted through the plant sample at the first wavelength; and
generate a second data signal indicative of the light transmitted through the plant sample at the second wavelength; and
a processor operably coupled with the first light source, the second light source, and the detector, wherein the processor is configured to generate a chlorophyll content output responsive to an optical/absolute relationship that is determined by an optical/absolute relationship defined by an equation selected from the group consisting of chlorophyll concentration being equal to:
about $-8+29*(CCI)^{0.80}$;
about $-19+39*(CCI)^{0.69}$;
about $-64+57*(CCI)^{0.68}$;
about $-84+79*(CCI)^{0.60}$;
about $-103+123*(CCI)^{0.47}$;
about $-121+129*(CCI)^{0.42}$;
about $-132+146*(CCI)^{0.43}$;
about $-150+162*(CCI)^{0.34}$;
about $-328+304*(CCI)^{0.26}$;
about $-334+316*(CCI)^{0.24}$;
about $-2204+2204*(CCI)^{0.04}$; and
about $-29+32*(CCI)^{0.74}$, wherein $$CCI = \frac{\% \text{ Transmission first wavelength}}{\% \text{ Transmission second wavelength}}.$$

8. The chlorophyll meter of claim 7, wherein the equation for chlorophyll concentration being equal to:
about $-8+29*(CCI)^{0.80}$ is for Sorghum ($C_4$);
about $-19+39*(CCI)^{0.69}$ is for Pepper;
about $-64+57*(CCI)^{0.68}$ is for Rice;
about $-84+79*(CCI)^{0.60}$ is for Wheat;
about $-103+123*(CCI)^{0.47}$ is for Soybean;
about $-121+129*(CCI)^{0.42}$ is for Maize ($C_4$);
about $-132+146*(CCI)^{0.43}$ is for Barley;
about $-150+162*(CCI)^{0.34}$ is for Kohlrabi;
about $-328+304*(CCI)^{0.26}$ is for Tomato;
about $-334+316*(CCI)^{0.24}$ is for Pea;
about $-2204+2204*(CCI)^{0.04}$ is for Waldman's Green Lettuce; and
about $-29+32*(CCI)^{0.74}$ is for Buttercrunch Lettuce.

9. A method for determining chlorophyll content of a plant sample, the method comprising:
emitting light at a first wavelength and a second wavelength into a plant sample with a chlorophyll meter;
detecting the light after passing through the plant sample;
generating, with a processor, an optical value responsive to a ratio of the percentage of transmitted light through the plant sample for the first wavelength and the second wavelength; and
determining, with the processor, chlorophyll content based on the optical value compared with an optical/absolute chlorophyll relationship, wherein the optical/absolute relationship is one of a plurality of different optical/absolute relationships that a user may select from for different species, and wherein the optical/absolute relationships used within the chlorophyll meter provide a variable, non-linear response for different plant species.

10. The method of claim 9, further comprising displaying the chlorophyll content in units of chlorophyll on the chlorophyll meter.

11. The method of claim 10, further comprising displaying the chlorophyll content data in SPAD units and in CCI units.

12. A method for determining chlorophyll content of a plant sample, the method comprising:
emitting light at a first wavelength and a second wavelength into a plant sample with a chlorophyll meter;
detecting the light after passing through the plant sample;
generating, with a processor, an optical value responsive to a ratio of the percentage of transmitted light through the plant sample for the first wavelength and the second wavelength;
determining, with the processor, chlorophyll content based on the optical value compared with an optical/absolute chlorophyll relationship, and wherein the optical/absolute relationship is one of a plurality of different optical/absolute relationships that a user may select from for different species; and
receiving inputs from a user for coefficients associated with an optical/absolute chlorophyll relationship that previously was not stored within the chlorophyll meter.

13. A portable optical chlorophyll meter, comprising:
a sampling head including a plurality of light sources configured to emit different wavelengths of through a plant sample;
a detector region including a detector having a field of view aligned with the sampling head to receive the light, the detector configured to detect the different wavelengths of light;
an electronic display; and
a processor operably coupled with the light sources and the detector, the processor configured to determine chlorophyll content of the plant sample based on an optical/absolute relationship that is selectable by the user from among optical/absolute relationships stored in memory for a plurality of different plant species, and to display the chlorophyll content on the electronic display in units of chlorophyll, wherein the optical/absolute relationships stored in memory for the plurality of different species include one or more of the following:

about $-76+85*(CCI)^{0.64}$ is for European Birch;
about $-98+93*(CCI)^{0.51}$ is for Lilac;
about $-95+96*(CCI)^{0.57}$ is for Norway Maple;
about $-128+106*(CCI)^{0.50}$ is for Quaking Aspen;
about $-144+113*(CCI)^{0.55}$ is for Purple Leaf Sand Cherry;
about $-124+117*(CCI)^{0.47}$ is for Crab Apple;
about $-120+135*(CCI)^{0.48}$ is for Paper Birch;
about $-160+144*(CCI)^{0.50}$ is for Crimson King Maple;
about $-150+150*(CCI)^{0.43}$ is for Japanese Maple;
about $-191+182*(CCI)^{0.38}$ is for Box Elder;
about $-486+477*(CCI)^{0.18}$ is for Forsythia;
about $-8+29*(CCI)^{0.80}$ is for Sorghum ($C_4$);
about $-19+39*(CCI)^{0.69}$ is for Pepper;
about $-64+57*(CCI)^{0.68}$ is for Rice;
about $-84+79*(CCI)^{0.60}$ is for Wheat;
about $-103+123*(CCI)^{0.47}$ is for Soybean;
about $-121+129*(CCI)^{0.42}$ is for Maize ($C_4$);
about $-132+146*(CCI)^{0.43}$ is for Barley;
about $-150+162*(CCI)^{0.34}$ is for Kohlrabi;
about $-328+304*(CCI)^{0.26}$ is for Tomato;
about $-334+316*(CCI)^{0.24}$ is for Pea;
about $-2204+2204*(CCI)^{0.04}$ is for Waldman's Green Lettuce; and
about $-29+32*(CCI)^{0.74}$ is for Buttercrunch Lettuce, wherein $$CCI = \frac{\%\ \text{Transmission first wavelength}}{\%\ \text{Transmission second wavelength}}.$$

14. The chlorophyll meter of claim 13, wherein the units of chlorophyll are expressed in at least one of micromoles per square meter ($\mu$mol m$^{-2}$) and milligrams per square meter (mg m$^{-2}$).

15. The chlorophyll meter of claim 13, wherein the optical/absolute relationship is a linear relationship within ±1% tolerance.

16. The chlorophyll meter of claim 13, wherein the chlorophyll content is determined based on at least one of a single measurement, an average multi-point measurement, and a standard deviation, according to a mode selectable by a user.

17. The chlorophyll meter of claim 13, wherein the detector region includes a removable field of view reducer that is configured to reduce a field of view for the detector from an outer field of view when the field of view reducer is not inserted.

* * * * *